(12) United States Patent
Uckun et al.

(10) Patent No.: US 6,337,348 B1
(45) Date of Patent: *Jan. 8, 2002

(54) OXY-VANADIUM (IV) COMPLEXES HAVING SPERMICIDAL ACTIVITY

(75) Inventors: Faith M. Uckun, White Bear Lake; Osmond D'Cruz, Maplewood; Wanhong Dong, St. Paul, all of MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/505,386

(22) Filed: Feb. 16, 2000

Related U.S. Application Data

(62) Division of application No. 09/187,115, filed on Nov. 5, 1998, now Pat. No. 6,245,808.

(51) Int. Cl.[7] .............................................. A61K 31/28
(52) U.S. Cl. ........................................ 514/492; 514/310
(58) Field of Search ................................. 514/492, 310

(56) References Cited

U.S. PATENT DOCUMENTS

| | | |
|---|---|---|
| 4,297,341 A | 10/1981 | Waller et al. |
| 4,322,399 A | 3/1982 | Ahmad et al. |
| 4,368,186 A | 1/1983 | Vickery et al. |
| 4,432,967 A | 2/1984 | Szymanski |
| 4,559,157 A | 12/1985 | Smith et al. |
| 4,588,581 A | 5/1986 | Schmolka |
| 4,608,387 A | 8/1986 | Kopf et al. |
| 4,608,392 A | 8/1986 | Jacquet et al. |
| 4,613,497 A | 9/1986 | Chavkin |
| 4,707,362 A | 11/1987 | Nuwayser |
| 4,795,425 A | 1/1989 | Pugh |
| 4,820,508 A | 4/1989 | Wortzman |
| 4,917,901 A | 4/1990 | Bourbon et al. |
| 4,938,949 A | 7/1990 | Borch et al. |
| 4,992,478 A | 2/1991 | Geria |
| 4,999,342 A | 3/1991 | Ahmad et al. |
| 5,013,544 A | 5/1991 | Chantler et al. |
| 5,021,595 A | 6/1991 | Datta |
| 5,069,906 A | 12/1991 | Cohen et al. |
| 5,387,611 A | 2/1995 | Rubinstein |
| 5,407,919 A | 4/1995 | Brode et al. |
| 5,512,289 A | 4/1996 | Tseng et al. |
| 5,595,980 A | 1/1997 | Brode et al. |
| 6,051,603 A * | 4/2000 | D'Cruz et al. .............. 514/492 |

FOREIGN PATENT DOCUMENTS

| | | |
|---|---|---|
| EP | 0 407 804 A1 | 6/1990 |
| WO | WO 97/47296 | 12/1997 |

OTHER PUBLICATIONS

Ghosh, Phalguni et al. Structural and Biological Characterization of a Novel Spermicidal Vanadium (IV) Complex: Bis (pi–Cyclopentadienyl)–N,N–diethyl Dithiocarbamato Vanadium(IV) Tetrafluoro Borate [VCp2(DeDtc)](BF4). J. of Inorg. Biochem. vol. 72, pp. 89–98 (Aug. 14, 1998).*

Aistars, A. et al., 1997, *Organometallics*, vol. 16, pp. 1994–1996 "Convenient Synthesis of Dichloro(oxo)(pentamethylcyclopentadienyl)vanadium(V), ($\eta$–$C_5Me_5$)V(O)$Cl_2$".

Albini, A. et al., 1987 *Cancer Research*, vol. 47, pp. 3239–3245 (Jun. 15, 1987) "A Rapid in Vitro Assay for Quantiating the Invasive Potential of Tumor Cells".

(List continued on next page.)

*Primary Examiner*—Michael G. Hartley
*Assistant Examiner*—Michael A. Willis
(74) *Attorney, Agent, or Firm*—Merchant & Gould

(57) ABSTRACT

Organometallic oxovanadium (IV) complexes having potent spermicidal activity, particularly those having at least one bidentate ligand. Preferred compounds are stable oxovanadium (IV) complexes having, as ancillary ligands linked via nitrogen or oxygen-metal bonds, bis and/or mono-1,10-phenanthroline; 2,2'-bipyridyl; or 2-hydroxyacetophenone.

70 Claims, 7 Drawing Sheets

OTHER PUBLICATIONS

Aubrecht, J. et al., 1999, *Toxicology and Applied Pharmacology*, vol. 154, No. 3, pp. 228–235 (Feb. 1, 1999) "Molecular Genotoxicity Profiles of Apoptosis–Inducing Vanadocene Complexes".

Casey, A.T. et al., 1974, *Aust. J. Chem*, vol. 27, pp. 757–768 "Dithiochelates of the Bis($\eta$–cyclopentadienyl)vanadium(IV) Moiety. II N,N–Dialkyldithiocarbamate and O,O'–Dialkyldithiophosphate Complexes".

Chen, D. et al., 1992, *Bopuxue Zazhi*, vol. 9 No. 1, pp. 25–44 "ESR studies on the oxovanadium phenanthroline complexes" (Abstract only).

Chen, D. et al., 1993, *Yingyong Huaxue*, vol. 10, No. 3, pp. 68–71 "ESR Spectroscopic Study of Oxovanadium Complexes with His and $\pi$–Acceptor Ligands".

Chen, D. et al., 1993, *Chinese Journal of Magnetic Resonance*, vol. 10, No. 3, pp. 287–294 (Sep. 1993) "Structure and ESR spectra of oxovanadium ternary complexes with aspartic acid and pi.–acceptor ligands".

Chen, D. et al., 1995, *Chines Journal of Applied Chemistry*, vol. 12, No. 2, pp. 59–62 (Apr. 1995) "Study on Structures and Spectra of Oxovanadium Complexes with Glu and Phen Ligands".

Chen, D. et al., 1999, *Journal of Magnetic Resonance*, vol. 16, No. 1, pp. 53–58 (Feb. 1999) "Structures and spectra of VO(II)–Met–Phen complexes".

Chou P., 1999, *Photochemistry and Photobiology*, vol. 70, No. 5, pp–745–750 "Direct Spectroscopic Evidence for $1\Delta_g O_2$ Production from the Photolysis of Vanadium(V)–Peroxo Complexes in Adqeous Solution".

Choukroun, R. et al., 1995, *Organometallics*, vol. 14, pp. 4471–4473 "Redox Properties of Cationic Vanadium (IV): $[Cp_2VCH_3(CH_3CN)][BPh_4]$".

Demsar, A. et al., 1984, *Journal of Fluorine Chemistry*, vol. 24, No. 3, pp. 369–375 (Mar. 1984) "Synthesis and the molecular and crystal structure of aquadifluorooxo (1, 10–phenanthrolino)vanadium(IV), $[VOF_2(H_2O)(1,10$–phenanthroline)]".

Edelman, G., 1994, *Progress in Brain Research*, vol. 101, Chapter 1, pp. 1–14 "Adhesion and counteradhesion: morphogenetic functions of the cell surface".

Eliopoulos, A. et al., 1995, *Biochemical Pharmacology*, vol. 50, No. 1, pp. 33–38 "Induction of the c–myc But Not the cH–ras Promoter by Platinum Compounds".

Filgueiras, C. et al., 1981, *Transition Met. Chem.*, vol. 6, pp. 258–260 "Complexes of Oxovanadium (IV) with Cyclic Nitrogen–Containing Ligands".

Heffetz, D. et al., 1990, *J. Biol. Chem.*, vol. 265, vol. 5, pp. 2896–2902 (Feb. 15, 1990) "The insulinomimetic Agents $H_2O_2$ and Vanadate Stimulate Protein Tyrosine Phosphorylation in Intact Cells".

Holmes, L., Jr, 1961, Ph.D. Thesis, LSU "Physical Chemical Studies on Inorganic Coordination Compounds. I. Metallic Complexes of Dimethylsulfoxide. II. Preparation and Spectral Studies of Vanadyl Complexes".

Islam, M. et al., 1992, *Journal of the Bangladesh Chemical Society*, vol. 5, No. 2, pp. 115–120 "Mixed Ligand Complexes of Phthalic Acid and Amine Bases".

King, B., 1965, *Academic Press, Inc.*, vol. 1, pp. 75–76 "Organomettallic Syntheses".

Kopf–Maier, et al., 1984, *Eur. J. Med. Chem—Chim. Ther.*, vol. 19, No. 4, pp. 347–352 "Tumorhemmung durch Metallocene: Titan–Komplexe des Typs $[TiCp_2XY]$ und $[TiCpX_2Y]$".

Kopf–Maier, P., 1987, *J. Cancer Res Clin Oncol*, vol. 113, pp. 342–348 "Tumor inhibition by titanocene complexes: Influence upon two xenografted human lung carcinomas".

Kopf–Maier, P. et al., 1987, *Arzneim.–Forsch./Drug Res.* vol. 37, pp. 532–534 "Tumor Inhibition by Titanocene Complexes".

Meirim, M. et al., 1984, *Transition Met. Chem.*, vol. 9, No. 9, pp. 337–338 (Sep. 1984) "A Chlorotitanocene Tetrachloroferrate Complex Stabilized by Acetonitrile Coordination".

Mosmann, T., 1983, *Journal of Immunological Methods*, vol. 65, pp. 55–63 "Rapid Colorimetric Assay for Cellular Growth and Survival: Application to Proliferation and Cytotoxicity Assays".

Narla, R. et al., 1998, *Clinical Cancer Research*, vol. 4, pp. 1405–1414 (Jun. 1998) 4–(3'–Bromo–4'hydroxylphenyl)–amino–6,7–dimethoxyquinazoline: A Novel Quinazoline Derivative with potent Cytotoxic Activity against Human Glioblastoma Cells.

Narla, R. et al., 1998, *Clinical Cancer Research*, vol. 4, pp. 2463–2471 (Oct. 1998) "Inhibition of Human Glioblastoma Cell Adhesion and Invasion by 4–(4'–Hydroxylphenyl)–amino–6,7–dimethoxyquinazoline (WHI–P131) and 4–(3'–Bromo–4"–hydroxylphenyl)–amino–6,7–dimethoxyquinazoline (WHI–P154)".

Orvig, C. et al., 1995, *metal ions in biological systems*, vol. 31, Ch. 17, pp. 595–616 "Vanadium Compounds as Insulin Mimics".

Perentesis, J. 1997, *Clinical Cancer Research*, vol. 3, pp. 347–355 (Mar. 1997) "Induction of Apoptosis in Multidrug–resistant and Radiation–resistant Acute Myeloid Leukemia Cells by a Recombinant Fusion Toxin Directed against the Human Granulocyte Macrophage Colony–stimulating Factor Receptor".

Quilitzsch, U. et al., 1979, *Inorganic Chemistry*, vol. 18, No. 3, pp. 869–871 "Kinetics of the Diperoxovanadate(V)–Monoperoxovanadate(V) Conversion in Percholoric Acid Media".

Savostina, V. M. et al., 1979, *Zh. Neorg. Khim.*, vol. 24, No. 1, pp. 41–45 "Study of the reaction of vanadium(III), vanadium(IV), and vanadium(V) with 1,10–phenanthroline".

Selbin, J., 1965, *Chemical Reviews*, vol. 65, No. 2, pp. 153–175 (Mar. 25, 1965) The Chemistry of Oxovanadium(IV).

Sharma C.L. et al., 1986, *Synth. React. Inorg. Met.–Org. Chem.*, vol. 16, No. 9, pp. 1261–1271 Preparation and Characterisation of Mixed Ligand Complexes of Titanium (III) and Vanadium (IV) with Imides and Heterocyclic Amines.

Stern, A. et al., 1993, *Biochem. Cell Biol.*, vol. 71, Nos. 3 & 4, pp. 103–112 (Mar.–Apr. 1993) "Vanadium as a modulator of cellular regulatory cascades and oncogene expression".

Thewalt, U. et al., 1986, *Journal of Organometallic Chemistry*, vol. 302, pp. 193–200 "Kationische Komplexe Mit Der $(\eta^5-C_5H_5)_2Ti^{IV}$–Baugruppe: Darstellung Und Struktur von $[(\eta^5-C_5H_5)_2Ti(bipy)]^{2+}(CF_3SO_3-)_2$ Und $[(\eta^5-C_5H_5)_2Ti(phen)]^{2+}(CF_3SO_3-)_2$".

Toney, J. et al., 1986, *J. Am. Chem. Soc.* 108:7263–7274 "Aqueous Coordination Chemistry of Vanadocene Dichloride, $V(\eta^5-C^5H^5)xCl_2$, with Nucleotides and Phosphoesters. Mechanistic Implications for a New Class of Antitumor Agents".

Tsiani, E. et al., 1997, *Trends in Endocrinol. Metab.*, vol. 8, No. 2 (Mar. 1997) "Vanadium Componds, Biological Actions and Potential as Pharmacological Agents".

Uckun, F.M. et al., 1995 *Science*, vol. 267, No. 5199, pp. 886–891 (Feb. 10, 1995) "Biotherapy of B–Cell Precursor Leukemia by Targeting Genistein to CD 19–Associated Tyrosine Kinases".

Uckun, F. et al., 1998, *Clinical Cancer Research*, vol. 4, pp. 901–912 (Apr. 1998) "Cytotoxic Activity of Epidermal Growth Factor–Genistein against Breast Cancer Cells".

Vassilev, A., 1999, *Journal of Biological Chemistry*, vol. 274, No. 3, pp. 1646–1656 (Jan. 15, 1999) "Bruton's Tyrosine Kinase as an Inhibitor of the Fas/CD95 Death–inducing Signaling Complex".

Vinklárek, J. et al., *Metal–Based Drugs*, vol. 4, No. 4, pp. 207–219 (1997) "Behaviour of the Antitumor Agent Vanadocene Dichloride in Physiological and Therapeutic Media, Blood Plasma and Human Blood—An EPR Study".

Waurzyniak, B. et al., 1997, *Clinical Cancer Research*, vol. 3, pp. 881–890 (Jun. 1997) "In Vivo Toxicity, Pharmacokinetics, and Antileukemic Activity of tXU (Anti–CD7)–Pokeweed Antiviral Protein Immunotoxin".

Aitken, et al., 1989, *Biol Reprod*, 41:183–197 "Generation of Reactive Oxygen Species, Lipid Peroxidation, and Human Sperm Function".

Aitken, et al., 1993, *J Reprod Fertil*, 97:441–450 "Use of a Xanthine Oxidase Free Radical Generating System to Investigate the Cytotoxic Effects of Reactive Oxygen Species on Human Spermatozoa".

Aitken, et al., 1994, *BioEssays*, 16:259–267 "Reactive Oxygen Species Generation and Human Spermatozoa: The Balance of Benefit and Risk".

Aitken, R. J., 1995, *Reprod. Fertil. Dev.*, 7:659–668 "Free Radicals, Lipid Peroxidation and Sperm Function".

Altamirano–Lozano, et al., 1997, *Med. Sci. Rev.*, 25:147–150 "Effect of some metal compounds on sperm motility in vitro".

Altamirano–Lozano, et al., 1996, *Teratogenesis, Carcinogenesis, and Mutagenesis*, 16:7–17 "Reprotoxic and Genotoxic Studies of Vanadium Pentoxide in Male Mice".

Alvarez, et al., 1987, *J Androl*, 8:338–348 "Spontaneous Lipid Peroxidation and Production of Hydrogen Peroxide and Superoxide in Human Spermatozoa".

Biggers, et al., 1971, *Methods in Mammalian Embryology*, Daniel, JC Jr. (ed.), San Francisco: Freeman, pp. 86–116 "The Culture of Mouse Embryos in vitro".

Bourinbaiar, et al., 1994, *Life Sci*, 54:PL 5–9 "Anti–HIV Effect of Gramicidin in vitro: Potential for Spermicide".

Burkman, L.J., 1991, *Fertil Steril*, 55:363–371 "Discrimination Between Nonhyperactivated and Classical Hyperactivated Motility Patterns in Human Spermatozoa Using Computerized Analysis".

Butler A., et al., 1989, *Inorganica Chimica Acta*, 163:1–3 "Reactivation of Vanadate–Inhibited Enzymes with Desferrioxamine B, a Vanadium (V) Chelator".

Byczkowski, et al., 1988, *Bull Environ Contam Toxicol*, 41:696–703 "Vanadium–Mediated Lipid Peroxidation in Microsomes from Human Term Placenta".

Carmichael ,A.J., 1990, *FEBS Lett*, 261:165–170 "Vanadyl–Induced Fenton–Like Reaction in RNA: an ESR and Spin Trapping Study".

Cossarizza, A. et al., 1993, *Biochem. Biophys. Res. Comm.*, 197:40–45 A new method for the cytofluorimetric analysis of mitochondrial membrane potential using the J–aggregate forming lipophilic cation 5,5',6,6'-tetrachloro-1,1',3,3'-tetraethylbenzimidazolcarbocyanine Iodide (JC–1).

D'Cruz, O.J. et al., 1992, *Fertil. Steril.*, 58:633–636 "Flow cytometric quantitation of the expression of membrane cofactor protein as a marker for the human sperm acrosome reaction".

D'Cruz, et al., 1995, *Biol Reprod*, 53:1118–1130 "$\beta_2$–Integrin (CD11b/CD18) is the Primary Adhesive Glycoprotein Complex Involved in Neutrophil–Mediated Immune Injury to Human Sperm".

D'Cruz, O.J. et al., 1996, *Biol. Reprod.*, 54:1217–1228 "Recombinant soluble human complement receptor type 1 inhibits antisperm antibody–and neutrophil–mediated injury to human sperm".

D'Cruz, O.J. et al., 1998, *Mol. Hum. Reprod.*, 4:683–693 "Spermicidal activity of chelated complexes of bis(cyclopentadienyl)vandium(IV)".

D'Cruz, O. et al., 1998, *Biol. Reprod.*, 58:1515–1526 "Spermicidal activity of metallocene complexes containing vanadium(IV) in humans".

D'Cruz, O. et al., Copyright 1999, *Chemical Abstracts*, 130, Abstract No. 262258:1page "Spermicidal activity of oxovanadium(IV) complexes of 1,10–phenanthroline, 2,2'-bipyridyl, 5'-bromo-2'-hydroxyacetophenone and derivatives in humans".

D'Cruz, O.J. et al., 1993, *Fertil. Steril.*, 59:876–884 "The expression of the complement regulators CD46, CD55, and CD59 by human sperm does not protect them from antisperm antibody– and complement–mediated injury".

D'Cruz, O.J. et al., 1998, *Adv. Reprod.*, 1:101–123 "Vanadocenes as a new class of effective spermicides".

de Lamirande et al., 1993, *Fertil. Steril.* 59:1291–1295 "Human sperm hyperactivation in whole semen and its association with low superoxide scavenging capacity in seminal plasma".

Djordjevic, 1995, *Metal Ions In Biological Systems*, Ref. 89, 31:595–615 "Antitumor Activity of Vanadium Compounds".

Dorer, et al., 1997, *Collect Czech Chem Comm*, 62:265–278 "ansa–Vanadocene Complexes–Syntheses, Structures and Ligand Exchange Reactions".

Doyle, et al., 1968, *Inorg Chem*, 7:2479–2484 "Pseudohalide and Chelate Complexes of Bis(cyclopentadienyl)vanadium(IV)".

Erlandsen, et al., 1989, *Scanning*, 11:169–175 "Membrane Fixation for High–Resolution Low–Voltage SEM: Studies on Giardia, Rat Spermatozoa, and Mouse Macrophages".

Gavrieli, et al., 1992, *J Cell Biol*, 119:493–501 "Identification of Programmed Cell Death in situ via Specific Labeling of Nuclear DNA Fragmentation".

Gibbons, et al., 1978, *Proc Natl Acad Sci USA*, 75:2220–2224 "Potent Inhibition of Dynein Adenosinetriphosphatase and of the Motility of Cilia and Sperma Flagella by Vanadate".

Hiort, C. et al., 1996, *Biochemistry*, 35:12354–12362 "Cleavage of DNA by the insulin–mimetic compound, $NH_4[VO(O_2)_2(phen)]$".

Hirao, T., 1997, *Chemical Rev.* 97:2707–2724 "Vanadium in modern organic synthesis".

Hyslop, P.A. et al., 1988, *The Journal of Biological Chemistry*, 263(4):1665–1675 "Mechanisms of Oxidant–mediated Cell Injury".

Jones, et al., 1979, *Fertil Steril*, 31:531–537 "Peroxidative Breakdown of Phospholipids in Human Spermatozoa: Spermicidal Properties of Fatty Acid Peroxides, and Protective Action of Seminal Plasma".

Keller, R.J. et al., 1988, *Archiv. Biochem. Biophys.*, 265:524–533 Vanadium and lipid peroxidation: evidence for involvement of vanadyl and hydroxyl radical.

Kessopoulou, E. et al., 1992, *J. Reprod. Fert.*, 94:463–470 "Origin of reactive oxygen species in human semen: spermatozoa or leucocytes?".

Klebanoff, S.J., 1992, *J. Infect. Dis.*, 165:19–25 "Effects of the spermicidal agent nonoxynol–9 on vaginal microbial flora".

Kopf–Maier, P. et al., 1987, *Chem. Rev.*, 87:1137–1152 Non–platinum–group metal antitumor agents: history, current status, and perspectives.

Kopf–Maier, et al., 1981, *Eur J Cancer*, 17:665–669 "Tumor Inhibition by Metallocenes: Activity Against Leukemias and Detection of the Systemic Effect".

Kopf–Maier, et al., 1983, *Chem Biol Interactions*, 44:317–328 "Tumor Inhibition by Metallocenes: Ultrastructural Localization of Titanium and Vanadium in Treated Tumor Cells by Electron Energy Loss Spectroscopy".

Kopf–Maier, et al., 1981, *Cancer Chemother Pharmacol*, 5:237–241 "In vitro Cell Growth Inhibition by Metallocene Dichlorides".

Kopf–Maier, et al., 1983, *J Cancer Res Clin Oncol*, 106:44–52 "Induction of Cell Arrest at $G_1/S$ and in $G_2$ After Treatment of Ehrlich Ascites Tumor Cells with Metallocene Dichlorides and cis–Platinum in vitro".

Kopf–Maier, et al., 1984, *Virchows Arch [Cell Pathol]*, 47:107–122 "Cytologic Observations on the Effects of Metallocene Dichlorides on Human Fibroblasts Cultivated in vitro".

Martin, et al., 1995, *J Exp Med*, 182:1545–1556 "Early Redistribution of Plasma Membrane Phosphatidylserine is a General Feature of Apoptosis Regardless of the Initiating Stimulus: Inhibition by Overexpression of Bcl–2 and Abl".

McLaughlin, et al., 1990, *J Am Chem Soc*, 112:8949–8952 "DNA–Metal Binding by Antitumor–Active Metallocene Dichlorides from Inductively Coupled Plasma Spectroscopy Analysis: Titanocene Dichloride Forms DNA–$Cp_2$ Ti or DNA–CpTi Adducts Depending on pH".

Moebus, et al., 1997, *Anticancer Res*, 17:615–821 "Antitumor Activity of New Organometallic Compounds in Human Ovarian Cancer Cell Lines and Comparison to Platin Derivatives".

Moran, et al., 1985, *J Organometallic Chemistry*, 291:311–319 "Synthesis and Characterization of Halogen and Pseudohalogen Derivatives of Substituted Vanadocenes".

Murthy, et al., 1988, *Inorg Chemica Acta*, 152:117–124 "Antitumor and Toxicologic Properties of the Organometallic Anticancer Agent Vanadocene Dichloride".

Nechay, B.R., 1982, *Annu. Rev. Pharmacol Toxicol.* 24:501–524 "Mechanisms of action of vanadium".

Niruthisard, et al., 1991, *Sex Transm Dis*, 18:176–179 "The Effects of Frequent Nonoxynol–9 Use on the Vaginal and Cervical Mucosa".

Ozawa, et al., 1989, *Chem Pharma Bull*, 37:1407–1409 "ESR Evidence for the Formation of Hydroxyl Radicals During the Reaction of Vanadyl Ions with Hydrogen Peroxide".

Petersen, et al., 1975, *J Am Chem Soc*, 97:6422–6433 "Synthesis and Structural Characterization by X–ray Diffraction and Electron Paramagnetic Resonance Single–Crystal Techniques of $V(\eta^5-C_5H_4CH_3)_2Cl_2$ and $Ti(\eta^5-C_5H_4CH_3)_2Cl_2$. A Study of the Spatial Distribution of the Unpaired Electron in a $V(\eta^5-C_5H_5)_2L_2$–type Complex".

Rao, B. et al., 1989, *Gamete Res.*, 24:127–134 "Lipid peroxidation in human spermatozoa as related to midpiece abnormalities and motility".

Roddy, et al., 1993, *Int J STD AIDS*, 4:165–170 "A Dosing study of Nonoxynol–9 and Genital Irritation".

Roshchin, et al. 1980, *Gig. Tr. Prof. Zabol.*, 5:49–51 (Abstract only) "Effect of *vanadium* on the generative function of laboratory animals".

Sakurai, et al., 1992, *Biochemical and Biophysical Research Communications*, 189:1090–1095 "DNA Cleavage by Hydroxyl Radicals Generated in a Vanadyl Ion–Hydrogen Peroxide System".

Sakurai, et al., 1995, *Biochem Biophys Res Commun*, 206:133–137 "Mechanism for a New Antitumor Vanadium Complex: Hydroxyl Radical–Dependent DNA Cleavage by 1,10–Phenanthroline–vanadyl Complex in the Presence of Hydrogen Peroxide".

Shi, et al., 1996, *Annals of Clinical and Laboratory Science*, 26:39–49 "Vanadium(IV) Causes 2'–Deoxyguanosine Hydroxylation and Deoxyribonucleic Acid Damage Via Free Radical Reactions".

Smiley, S.T. et al., 1991, *Proc. Natl. Acad. Sci. USA*, 88:3671–3675 "Intracellular heterogeneity in mitochondrial membrane potentials revealed by J–aggregate–forming lipophilic cation JC–1".

Teebor, G.W. et al., 1988, *Int. J. Radiat. Biol.*, 54:131–150 "The repairability of oxidative free radical mediated damage to DNA: a review".

Thewalt, et al., 1995, *Transition Metal Chem*, 10:393–395 "The Crystal and Molecular Structure of Acetonitrilechlorodicyclopentadienyltitanium Tetrachloroferrate (III). Some Mössbauer and X–Ray Photoelectron Spectroscopic Data".

Toney, et al., 1985, *J Am Chem Soc*, 107:947–953 "Hydrolysis Chemistry of the Metallocene Dichlorides $M(\eta^5-C_5H_5)_2Cl_2$, M = Ti, V, Zr. Aqueous Kinetics, Equilibria, and Mechanistic Implications for a New Class of Antitumor Agents".

Tryphonas, et al., 1984, *Toxicol Lett*, 20:289–295 "Morphologic Evidence for Vaginal Toxicity of Delfen Contraceptive Cream in the Rat".

Tryphonas, et al., 1986, *Toxicol*, 39:177–186 "Effects of the Spermicide Nonoxynol–9 on the Pregnant Uterus and the Conceptus of Rat".

van Engeland, M. et al, 1998, *Cytometry*, 31:1–9 "Annexin V–affinity assay: A review on an apoptosis detection system based on phosphatidylserine exposure".

Vermes, et al ., 1995, *J Immunol Meth*, 184:39–51 "A Novel Assay for Apoptosis. Flow Cytometric Detection of Phosphatidylserine Expression on Early Apoptotic Cells Using Fluorescein Labelled Annexin V".

Wilborn, et al., 1983, *Fertil Steril*, 39:717–719 "Scanning Electron Microscopy of Human spermatozoa After Incubation with the Spermicide Nonoxynol–9".

Wilkinson, et al., 1954, *J Am Chem Soc*, 76:4281–4284 "Bis–cyclopentadienyl Compounds of Ti, Zr, V, Nb, and Ta".

Wu, C., 1998, *Science News*, 6:359 "New spermicides stop cell gently".

Younes, et al., 1991, *Toxicology*, 66:63–74 "Vanadate–Induced Toxicity Towards Isolated Perfused Rat Livers: The Role of Lipid Peroxidation".

Zamzami, N. et al., 1995, *J. Exp. Med.*, 181:1661–1672 "Reduction in mitochondrial potential constitutes an early irreversible step of programmed lymphocyte death in vivo".

Asami, S. et al., Jun. 1, 1996, *Cancer Res.*, 56:2546–2549 "Increase of a type of oxidative DNA damage, 8–hydroxyguanine, and its repair activity in human leukocytes by cigarette smoking".

D'Cruz, O.J. et al., Aug. 1998, *Book of Abstracts*, 216th ACS National Meeting, See 336, "Vanadium (IV)–Containing Metallocenes Induce Cytotoxicity and Apoptosis in Human Testicular Cancer Cell Lines".

Ghosh, P. et al., 1998, *J. Inorg. Biochem.* vol. 72, Nos. 1, 2 (in press) "Structural and biological characterization of a novel spermicidal vanadium(IV) complex: Bis($\pi$–cyclopentadienyl)–,N,N–diethyl dithiocarbamato vanadium(IV) tetrafluoro borate, [VCp$_2$(DeDtc)(BF$_4$)]".

Kopf–Maier, et al., 1988, *Structure and Bonding*, 70:103–185 "Transition and Main–Group Metal Cyclopentadienyl Complexes: Preclinical Studies on a Series of Antitumor Agents of Different Structural Type".

Kopf–Maier, et al., 1993, In: Kepper BK (ed.), *Metal Complexes in Cancer Chemotherapy*, New York: VCH Publishers, pp. 259–296 "Antitumor bis(cyclopentadienyl) Metal Complexes".

Kuo et al., 1996, In: Sigel H. (ed.), *Metal Ions in Biological Systems*, pp. 53–85 "Metallocene Interactions with DNA and DNA–Processing Enzymes".

Macara I.G., 1980, Trends Biochem Sci, 5:92–94 "Vanadium—An Element in Search of a Role".

Stoffel, et al., *Molecular Reprod Develop* 1993; 34:175–182 "Improved Preservation of Rat Epididymal Sperm for High–Resolution Low–Voltage Scanning Electron Microscopy (HR–LVSEM)".

Wilkinson, G., 1982, *Comprehensive Organometallic Chemistry*, New York, Pergamon, 3:554–646 "Zirconium and Hafnium: Introduction".

* cited by examiner

VO(phen)

VO(phen)$_2$

VO(Me$_2$-phen)

VO(Me$_2$-phen)$_2$

VO(Cl-phen)

VO(Cl-phen)$_2$

VO(bipy)

VO(bipy)$_2$

VO(Me$_2$-bipy)

VO(Me$_2$-bipy)$_2$

VO(Br,OH-acph)$_2$

OXY-VANADIUM (IV) COMPLEXES HAVING SPERMICIDAL ACTIVITY

This application is a divisional of application Ser. No. 09/187,115, filed Nov. 5, 1998, U.S. Pat. No. 6,245,808, which application(s) are incorporated herein by reference.

FIELD OF THE INVENTION

This invention relates to compositions containing oxy-vanadium (IV). More particularly, the invention relates to oxy-vanadium (IV) containing complexes having spermicidal activity.

BACKGROUND OF THE INVENTION

The known spermicidal agents, nonoxynol-9 and gramicidin, exert their effects via a detergent-like ability to damage the sperm plasma membrane, perturb its conformation and destroy its semi-permeable nature thereby impairing the sperm motility and egg fertilizing functions (Wilborn, et al., *Fertil Steril* 1983; 39:717–719; Bourinbaiar, et al., *Life Sci* 1994; 54:PL 5–9). Because of their non-specific membrane disruptive properties, such vaginal spermicides have been shown to damage the cervicovaginal epithelium, as well, which may lead to a lower degree of protection from sexually transmitted diseases (Niruthisard, et al., *Sex Transm Dis* 1991; 18:176–179). A novel vaginal contraceptive preferably does not function with the non-specific membrane toxicity mediated by detergent-type action of the currently available vaginal contraceptives.

Vanadium is a physiologically essential element which can be found in one to five (I to V) oxidation states. Several inorganic salts containing vanadium with oxidation state +4 (IV) have been shown to function as modulators of cellular redox potential and to exert pleiotropic effects in multiple biological systems by catalyzing the generation of reactive oxygen intermediates. See, for example, Shi, et al., *Ann Clin Lab Sci* 1996; 26:390–49; Byczkowski, et al., *Bull Environ Contam Toxicol* 1988; 41:696–703; Younes, et al., *Toxicology* 1991; 66:63–74, and Sakurai, et al., *Biochem Biophys Res Commun* 1995; 206:133–137. Reactive oxygen intermediates have been reported to affect sperm motility by a combination of peroxidation of membrane lipids and proteins (Aitken, et al., *Biol Reprod* 1989; 40:183–197; Jones, et al., *Fertil Steril* 1979; 31:531–537). Peroxidative damage to the sperm plasma membrane is an important pathophysiological mechanism in the onset of male infertility (Aitken, et al., *BioEssays* 1994; 16:259–267). It has also been shown that superoxide radicals generated by the action of xanthine oxidase exert a direct, suppressive effect on many aspects of sperm function (Aitken, et al., *J. Reprod. Fertil.* 1993; 97:441–450). Sperm are thought to be particularly susceptible to oxidative stress by virtue of their high content of unsaturated fatty acids and their relative paucity of cytoplasmic enzymes for scavenging the reactive oxygen intermediates that initiate lipid peroxidation (Alvarez, et al., *J Androl* 1987; 8:338–348).

There is a need for new spermicidal compounds for contraceptive purposes. The ability of vanadium (IV) containing organometallic complexes to catalyze the generation of reactive oxygen species and the spermicidal activity of these agents was described in copending patent application U.S. Ser. No. 09/008,898, which is hereby incorporated by reference for all purposes.

Metallocene complexes containing vanadium (IV) as the central metal ion within the tetrahedral bis(cyclopentadienyl) [$Cp_2$] metal complex (vanadocene) have potent spermicidal activity against human sperm (*Biol Reprod* 58:1516,1998; *Molec Hum Reprod* 4:683, 1998). The spermicidal activity was dependent on vanadium (IV) as the central metal ion within the $Cp_2$-metal complex, but the various diacido groups and bidentate ligands coordinated to the $Cp_2$-vanadium (IV) moiety also significantly modulated the spermicidal potency.

SUMMARY OF THE INVENTION

Organometallic complexes containing oxovanadium (IV) (VO) have now been found to have potent, concentration-dependent spermicidal activity at micromolar concentrations. Preferred oxovanadium complexes of the invention are complexes having at least one bidentate ligand. Suitable bidentate ligands include N,N'; N,O; and O,O' bidentate ligands.

The spermicidal activity of oxovanadium (IV) complexes was found to be irreversible, since the treated sperm underwent apoptosis, as determined by the flow cytometric quantitation of mitochondrial membrane potential, surface Annexin V binding assay, and in situ DNA nick-end labeling of sperm nuclei. The percentages of apoptotic sperm quantitated by these flow cytometric assays correlated well with the spermicidal potency of oxovanadium (IV) complexes. These results provide unprecedented evidence that the spermicidal and apoptosis-inducing properties of diverse oxovanadium (IV) complexes is due to vanadium (IV) as the central metal ion within the oxovanadium (IV) complex. The oxovanadium (IV) complexes typically included at least one bidentate ligand within the complex. Suitable bidentate ligands include N,N'; N,O; and O,O' bidentate ligands. Examples of suitable bidentate ligands include bipyridyl, bridged bipyridyl and acetophenone ligands modulating the spermicidal potency. One example of a bridged bipyridyl includes phenanthroline. These novel oxovanadium (IV) complexes, and particularly the bromo-hydroxyacetophenone complex [OV(Br,OH-acph)$_2$], are useful as contraceptive agents.

Accordingly, the present invention includes spermicidal oxovanadium complexes, as well as contraceptive compositions containing a spermicidal effective amount of an oxovanadium IV complex and a pharmaceutically acceptable carrier, diluent or vehicle. The spermicidal compounds of the invention include organometallic oxovanadium (IV) complexes. Preferably, the oxovanadium (IV) is complexed with at least one bidentate ligand.

One suitable embodiment of the invention having a bidentate ligand wherein the bidenate ligand is a bipyridyl has the general formula I, shown below:

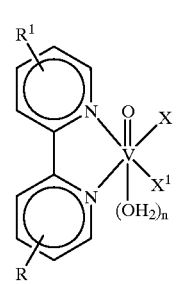

(I)

where R and $R^1$ are the same or different and are independently selected from: H, lower alkyl, halogen, lower alkoxy, halogenated alkyl, cyano, carboalkoxy (e.g. $C_2$–$C_6$) and nitro; X and $X^1$ are the same or different and are independently selected from: monodenate and bidentate ligands; and n is 0 or 1.

Another suitable embodiment of the invention having a bidentate ligand wherein the bidentate ligand is a bridged bipyridyl has the general formulae IV, shown below:

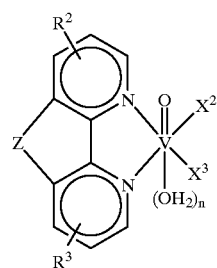

(IV)

where $R^2$ and $R^3$ are the same or different and are selected from H, lower alkyl, halogen, lower alkoxy, halogenated alkyl, cyano, carboalkoxy (e.g. $C_2$–$C_6$) and nitro; $X^2$ and $X^3$, are the same or different and are selected from monodentate and bidentate ligands; Z is selected from O, $CH_2$, $CH_2$—$CH_2$, and $CH=CH$; and n is 0 or 1.

Another suitable embodiment of the invention having a bidentate ligand wherein the bidentate ligand is a bridged bipyridyl, and the bridged bipyridyl is phenanthroline, has the general formula II, shown below:

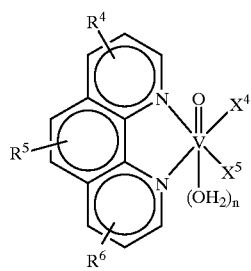

(II)

where $R^4$, $R^5$ and $R^6$ are the same or different and are independently selected from: H, lower alkyl, halogen, lower alkoxy, halogenated alkyl, cyano, carboalkoxy (e.g. $C_2$–$C_6$) and nitro; $X^4$ and $X^5$ are the same or different and independently selected from: monodentate and bidentate ligands; and n is 0 or 1.

Another suitable embodiment of the invention having a bidentate ligand wherein the bidentate ligand is an O,O' bidentate ligand, and the complex has the general formulae III, is shown below:

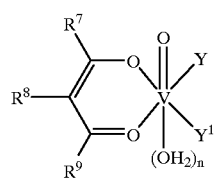

(III)

where $R^7$ and $R^9$ are the same or different and are independently selected from: H, lower alkyl, lower alkoxy, and halogenated alkyl; $R^8$ is selected from H, lower alkyl, halo, lower alkoxy, and halogenated alkyl; Y and $Y^1$ are the same or different and independently selected from the group consisting of: monodentate and bidentate ligands; and n is 0 to 1.

DETAILED DESCRIPTION

Figure 1:
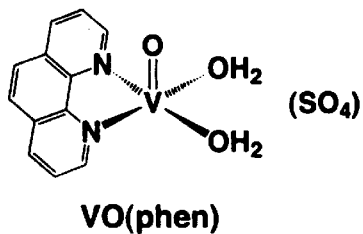
FIG. 1 is a structural drawing of a representative compounds V–XV of the invention.
Figure 1:
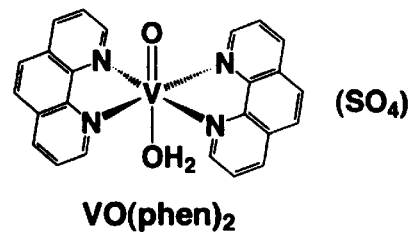
Figure 1:
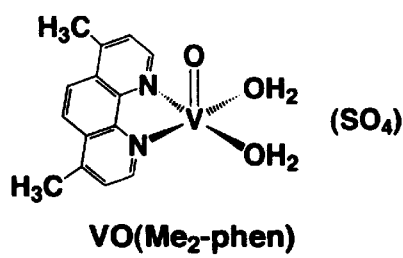
Figure 1:
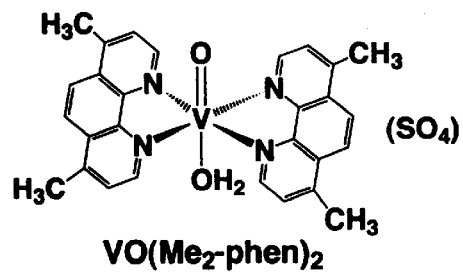
Figure 1:
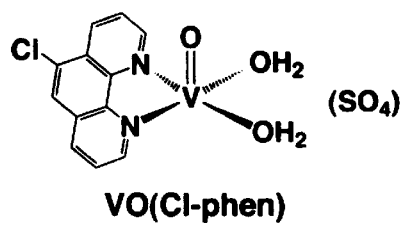
Figure 1:
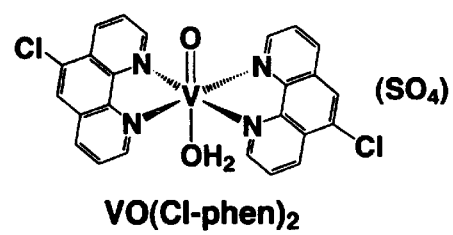
Figure 1:
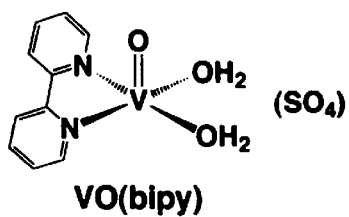
Figure 1:
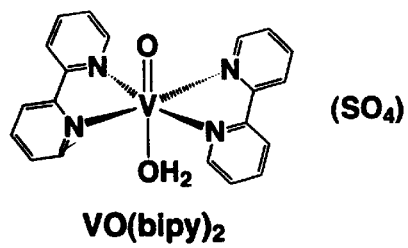
Figure 1:
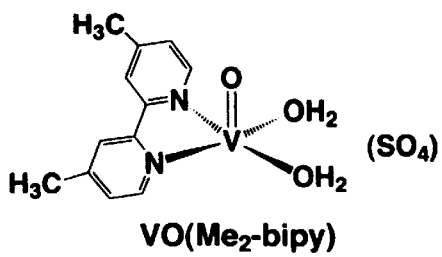
Figure 1:
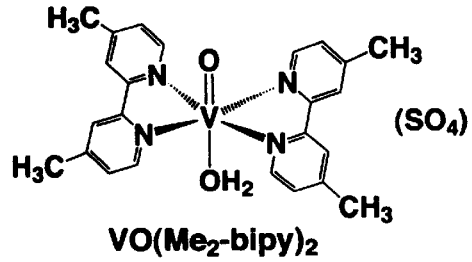
Figure 1:
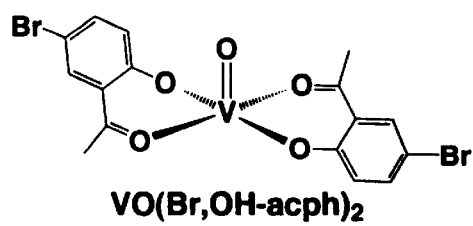

As used herein, the following definitions define the stated terms:

"Organometallic compound" is an organic compound comprised of a metal attached directly to carbon (R—M).

"Coordination compound" is a compound formed by the union of a central metal atom or ion with a nonmetal atom, ion or molecule called a ligand or complexing agent.

"Ligand" or a "complexing agent" is a molecule, ion or atom that is attached to the central metal atom or ion of a coordination compound.

"Monodentate ligand" is a ligand having a single donor atom coordinated to the central metal atom or ion.

"Bidentate ligand" is a ligand having two donor atoms coordinated to the same central metal atom or ion.

"Oxovanadium (IV) complex" is a coordination compound including vanadium as the central metal atom or ion, and the vanadium has an oxidation state of +4 (IV), and is double bonded oxygen.

The present invention concerns or organometallic oxovanadium complexes, and the finding that such oxovanadium complexes have potent and selective spermicidal activity, and are particularly active and stable spermicidal agents.

Another aspect of the present invention is a method of contraception including the step of contacting sperm with a spermicidal effective amount of an oxovanadium IV complex.

Vanadium

Vanadium is a physiologically essential element that can be found in both anionic and cationic forms with oxidation states ranging from –3 to +5 (I–V). This versatility provides unique properties to vanadium complexes. In particular, the cationic form of vanadium complexes with oxidation state +4 (IV) have been shown to function as modulators of cellular redox potential, regulate enzymatic phosphorylation, and exert pleiotropic effects in multiple biological systems by catalyzing the generation of reactive oxygen species (ROS). Besides the ability of vanadium metal to assume various oxidation states, its coordination chemistry also plays a key role in its interactions with various biomolecules. In particular, organometallic complexes of vanadium (IV) linked to bis(cycopentadienyl) moieties or vanadocenes exhibit antitumor properties both in vitro and in vivo primarily via oxidative damage.

Human Sperm

Human sperm are known to be exquisitely sensitive to oxidative stress due to the high content of polyunsaturated fatty acids in their cell membranes, the low levels of cytoplasmic enzymes (superoxide dismutase, catalase, and gluthathione peroxidase) for scavenging the reaction oxygen species (ROS) intermediates, the initiate lipid peroxidation, and reduced activity of repair enzymes (exonucleases, endonucleases, glycosidases, and polymerases) to recover from oxidative damage. Reactive oxygen species such as a hydrogen peroxide ($H_2O_2$) and hydroxyl radicals (*OH) have been shown to affect sperm motility by a combination of peroxidation of membrane lipids and proteins. Oxidative damage to sperm proteins, carbohydrates, and DNA is an important pathophysiological mechanism in the onset of male infertility. It has also been shown that superoxide radicals generated by the action of xanthine oxidse exert a direct, suppressive effect on sperm function, including loss of motility, impaired capacitation, and sperm-egg interaction.

Our recent studies of 12 monodentate and 7 bidentate bis(cyclopentadienyl)vanadium (IV) complexes showed that these vanadocenes have potent spermicidal and apoptosis-inducing properties against human sperm. In fact, very short (<1 minute) exposure to vanadocenes at nanomolar to micromolar concentrations was sufficient to induce complete sperm motility less, whereas, prolonged exposure of sperm to millimolar concentrations of inorganic vanadium (oxidation state IV and V) salts had no effect on sperm motility (see copending patent application U.S. Ser. No. 09/008,898). Furthermore, none of the other metallocenes (oxidation state IV) containing titanium, zirconium, molybdenum, or hafnium exhibited spermicidal activity.

Since the redox potential and the stability of organovanadium complexes are greatly affected by the complexed ligands, different ligands were selected to test their effects on the spermicidal activity and stability. Diverse complexes were synthesized, containing mono and bidentate ligands complexed with the central vanadium (IV) by carbon-, nitrogen-, or oxygen- metal bonds.

The stability of organometallic complexes with monodentate ligands in aqueous solutions was found to be improved by chelating effects of certain bidentate ligands, particularly dithiocarbamate and acetylacetonate (D'Cruz et al., 1998, *Mol. Hum. Reprod.* 4:683–693). Stable oxovanadium (IV) complexes were synthesized having, as ancillary ligands linked via nitrogen or oxygen-metal bonds, bis and/or mono-1,10-phenanthroline (phen); 2,2'- bipyridyl (bipy); or 2-hydroxyacetophenone (acph). Specific compounds included the following:

| phen | bipy | acph |
|---|---|---|
| VO(phen) | VO(bipy) | VO(Br,OH-acph)$_2$ |
| VO(phen)$_2$ | VO(bipy)$_2$ | |
| VO(Me$_2$-phen) | VO(Me$_2$-bipy) | |
| VO(Me$_2$-phen)$_2$ | VO(Me$_2$-bipy)$_2$ | |
| VO(Cl-phen) | | |
| VO(Cl-phen)$_2$ | | |

The phenanthroline complex of peroxivanadate potentiates the generation of ROS in cells (Sakurai et al., 1995, *BBRC* 206:133–137). These compounds were synthesized and examined for potential spermicidal activity using computer-assisted sperm analysis. (CASA). Results presented below provide unprecedented evidence that oxovanadium complexes, including oxovanadium IV-bound to phenanthroline, bipyridyl and 2-hydroxyacetophenone as ancillary ligands and their derivatives are potent spermicidal agents and also induce apoptosis in human sperm.

Compounds

Compounds of the invention include oxovanadium (IV) containing organometallic complexes having spermicidal activity. Preferred the oxovanadium (IV) complexes include at least one bidentate ligand. Suitable bidentate ligands include N,N'; N,O: and O,O' bidentate ligands. Examples of suitable bidentate ligands include bipyridyl, bridged bipyridyl, and acetophenone. Particularly, preferred oxovanadium compounds of the invention are those having the formulas I, II, III, and IV shown and described below.

A suitable embodiment of the invention includes a bidentate ligand wherein the bidentate ligand is a bipyridyl and the oxovanadium IV complex has the general formulae I, below:

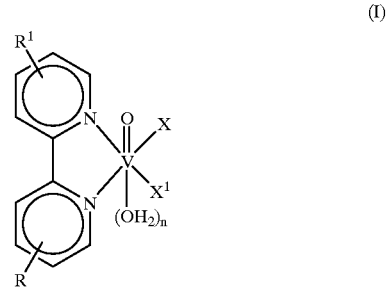

(I)

where R and $R^1$ are the same or different and are independently selected from: H, lower alkyl, halogen, lower alkoxy, halogenated alkyl, cyano, carboalkoxy (e.g. $C_2$–$C_6$) and nitro; X and $X^1$ are the same or different and are independently selected from: monodentate and bidentate ligands; and n is 0 or 1.

Another suitable embodiment of the invention has a bidentate ligand wherein the bidentate ligand is a bridged bipyridyl and the oxovanadium IV complex has the general formulae IV, below:

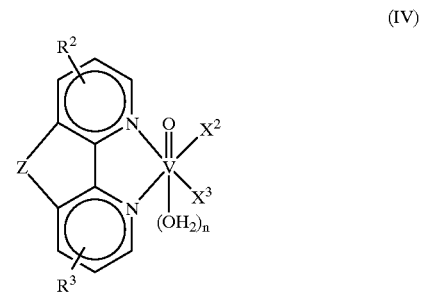

(IV)

where $R^2$ and $R^3$ are the same or different and are selected from H, lower alkyl, halogen, lower alkoxy, halogenated alkyl, cyano, carboalkoxy (e.g. $C_2$–$C_6$) and nitro; $X^2$ and $X^3$, are the same or different and are selected from monodentate and bidentate ligands; Z is selected from O, $CH_2$, $CH_2$—$CH_2$, and CH=CH; and n is 0 is 1.

Another suitable embodiment of the invention has a bidentate ligand wherein the bidentate ligand is a bridged bipyridyl, and the bridged bipyridyl is phenanthroline, and the oxovanadium IV complex has the general formulae II, below:

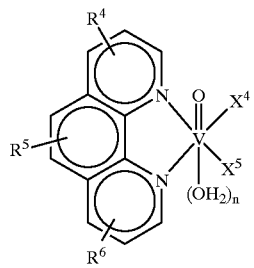

(II)

where $R^4$, $R^5$ and $R^6$ are the same or different and are independently selected from: H, lower alkyl, halogen, lower alkoxy, halogenated alkyl, cyano, carboalkoxy (e.g. $C_2$–$C_6$) and nitro; $X^4$ and $X^5$ are the same or different and independently selected from: monodentate and bidentate ligands; and n is 0 or 1.

Another suitable embodiment of the invention has a bidentate ligand wherein the bidentate ligand is an O,O' bidentate ligand, the oxovanadium IV complex has the general formulae III, below:

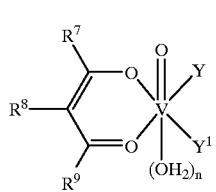

(III)

where $R^7$, and $R^9$ are the same or different and are independently selected from: H, lower alkyl, lower alkoxy, and halogenated alkyl; $R^8$ is selected from H, lower alkyl, halo, lower alkoxy, and halogenated alkyl; Y and $Y^1$ are the same or different and independently selected from the group consisting of: monodentate and bidentate ligands; and n is 0 or 1.

Preferred monodentate ligands for the oxovanadium complex include $H_2O$, halides and carboxylates. Preferred bidentate ligands include N,N' bidentate ligands, N, O bidentate ligands, and O, O' bidentate ligands. Examples of suitable N, N' bidentate ligands include diamines and other such known suitable N, N' bidentate ligands. Examples of diamines include bipyridal, derivatives of bipyridal, bridged bipyridal, such as phenanthroline, derivatives of phenanthroline, and other such compounds. Examples of suitable N, O bidentate ligands include amino acids and Schiff base type groups. Examples of suitable O, O' bidentate ligands include dicarboxylate, 2-hydroxyacetophenone, acetylacetone type and catechol type groups.

Particularly useful compounds of the invention are those shown in FIG. 1, compounds V–XV.

Spermicidal Use in Mammals

The spermicidal compositions of the present invention are suitable for use in mammals. As used herein, the term "mammals" means any class of higher vertebrates that nourish their young with milk secreted by mammary glands, e.g., humans, rabbits and monkeys.

The spermicides useful in accordance with the present invention include the above-mentioned oxovanadium complexes where the vanadium metal has an oxidation state of +4.

Thus, the contraceptive compositions of the present invention contain one of the above-mentioned organometallic oxovanadium complexes. The total amount of spermicide thereof will typically range from about 0.05 to 0.5 weight percent based on the weight of the contraceptive composition. Preferably, the amount of spermicide employed will be that amount necessary to achieve the desired spermicidal results. Appropriate amounts can be determined by those skilled in the art. Preferably, the amount of the spermicide employed, a spermicidal effective amount, will comprise from about 0.0025 to 0.025 weight percent, and more preferably from about 0.05 to 0.5 weight percent, based on the weight of the contraceptive composition.

When used in vivo to selectively kill testicular germ cells of testicular germ cell tumors, the administered dose is that effective to have the desired effect, e.g., sufficient to kill essentially all normal germ cells for chemical castration, or sufficient to reduce or eliminate a testicular cell tumor. The appropriate dose can be extrapolated using known methods and relationships. A useful dose will vary with the desired effect, the mode of administration, and the composition administered. In general, the desired dose will be in the range of 1–25 mg/kg body weight.

The compositions of the invention contain not only the spermicide but necessarily pharmaceutically acceptable carriers, diluents or vehicles, i.e., one that appropriately delivers oxovanadocene complexes to a site for contact with sperm or germ cells and provides spermicidal and/or anti-germ cell activity.

One advantageous component in the pharmaceutical composition for administration of a spermicide is a polymeric delivery component as described in U.S. Pat. No. 5,595,980, which patent is incorporated herein by reference. It has been found that such polymeric delivery component enhances effectiveness of a spermicide and reduces vaginal irritation on administration.

In addition to the polymeric component, the balance of the contraceptive compositions, i.e., typically from about 0.1 to 99.8% and often about 50 to 99.8 weight percent, may optionally comprise one or more cosmetic ingredients. Such cosmetic ingredients are known to those skilled in the art and are often referred to in the art as diluents, solvents and adjuvants. Typically cosmetic ingredients include, for example; water, ethyl alcohol, isopropyl alcohol, glycerin, glycerol propylene glycol, sorbitol and other high molecular weight alcohols. In addition, contraceptive compositions may contain minor amounts, e.g. from about 0.1 to 5% weight based on the weight of the contraceptive compositions, of other additives, such as, for example; stabilizers, surfactants, menthol, eucalyptus oil, other essential oils, fragrances, and the like. Polyoxyethylene 20 sorbitan monolaurate is a preferred stabilizer for use in the compositions. Details concerning the selection and amounts of cosmetic ingredients, other additives, and blending procedures are known to those skilled in the art.

The contraceptive compositions of the present invention may be delivered to the vagina of a mammal by any means known to those skilled in the art. Typical forms for delivery of the compositions include, for example; creams, lotions, gels, foams, sponges, suppositories and films. In addition, the compositions of the present invention may be used as personal care lubricants, such as, for example, condom lubricants, and the like. Such lubricants may comprise commonly known ingredients such as, for example: humectants; e.g., glycerin, sorbitol, mannitol, glycols and glycol ethers; buffers, e.g., glucono-d-lactone; germicides or bactericides; e.g., chlorhexidine gluconate; preservatives, e.g., methylparaben; viscosifiers; e.g., hydroxyethyl cellulose, etc.; other adjuvants; e.g., colors and fragrances; in addition to the compositions of the present invention. Those skilled in the art will recognize that the physical properties, e.g., viscosity, of such delivery forms may vary widely. For example, the viscosity of gel form of the composition of the present invention, e.g., 150,000 centipoise, may be substantially higher than the viscosity of lotion form of the composition of the present invention e.g., 100 centipoise. The contraceptive compositions may be located within a condom for example. Further details concerning the materials, ingredients, proportions and procedures of such delivery forms are known to those skilled in the art.

The contraceptive compositions of the present invention are preferably administered to the vagina of the mammal in a dosage which is effective to immobilize sperm present in the vagina and/or to inhibit their penetration in cervical mucus. Typical dosages range between about 0.0001 to 0.001 grams of the compositions per kilogram of body weight of the mammal.

Inter-vaginal devices may also be used to aid in the administration of the spermicide as described in U.S. Pat. No. 5,069,906.

In administration the spermicide in the form of the above compositions, the compositions may also be formulated to release the spermicide both rapidly and with a prolonged release of the drug. Such a formation providing both rapid and prolonged release has been described in U.S. Pat. No. 4,707,362, which patent is also incorporated herein.

In administering the spermicide in vivo, it is understood that multiple delivery methods are available, including injection both systemic and local. The preferred method of delivery is local, e.g., intratesticular injection. Where appropriate, the composition may be directly injected into a testicular germ cell tumor mass.

The invention may be further clarified by reference to the following Examples, which serve to exemplify some of the preferred embodiments, and not to limit the invention.

EXAMPLES

Example 1

Oxovanadium (IV) Complexes Containing 1,10-Phenanthroline, 2,2'-Bipyridyl or 5'-Bromo-2'-Hydroxyacetophenone and Derivatives Materials and Methods The chemical structures of the various mono and bis 1,10-phenanthroline, 2,2'-bipyridyl and 2-hydroxyacetophenone complexes of oxovanadium (IV) synthesized and analyzed in this study are depicted in FIG. 1. The cationic complexes synthesized and tested with 1,10-phenanthroline (phen), 2,2'-bipyridyl (bipy) and their derivatives as ancillary ligands with general formulas of [VO(L)(H$_2$O)$_2$](SO$_4$) and [VO(L)$_2$(H$_2$O)](SO$_4$) (L=ligand) are:

(1) [(VO(phen)]=(diaqua)(1,10-phenanthroline) oxovanadium (IV) sulfate;

(2) [VO(phen)$_2$]=(aqua)bis(1,10-phenanthroline) oxovanadium (IV) sulfate;

(3) [VO(Me$_2$-phen)]=(diaqua)(4,7-dimethyl-1,10-phenanthroline)oxovanadium (IV) sulfate;

(4) [VO(Me$_2$-phen)$_2$]=(aqua)bis(4,7-dimethyl-1,10-phenanthroline)oxovanadium (IV) sulfate;

(5) [VO(Cl-phen)]=(diaqua)(5-chloro-1,10-phenanthroline)oxovanadium (IV) sulfate;

(6) [VO(Cl-phen)$_2$]=(aqua)bis(5-chloro-1,10-phenanthroline)oxovanadium (IV) sulfate;

(7) [VO(bipy)]=(diaqua)(2,2'-bipyridyl)oxovanadium (IV) sulfate;

(8) [VO(bipy)$_2$]=(aqua)bis(2,2'-bipyridyl)oxovanadium (IV) sulfate;

(9) [VO(Me$_2$-bipy)]=(diaqua)(4,4'-dimethyl-2,2'-bipyridyl)oxovanadium (IV) sulfate;

(10) [VO(Me$_2$-bipy)$_2$]=(aqua)bis(4,4'-dimethyl-2,2'-bipyridyl)oxovanadium (IV) sulfate;

(11) [VO(Br,OH-acph)$_2$]=bis(5'-bromo-2'-hydroxyacetophenone)oxovanadium (IV)); and

(12) 5'-bromo-2'-hydroxyacetophenone was synthesized as a neutral complex.

Chemical Synthesis:

The 9 novel oxovanadium (IV) complexes were synthesized based on previously published chemistry of VO(phen) and VO(phen)$_2$ complexes (Sakurai et al., 1995, *BBRC* 206:133–137). Briefly, these complexes were synthesized by reacting an aqueous solution of vanadyl sulfate with an ethanol solution of a chloroform solution of the ligands. The complexes purified from chloroform, ether and/or water were characterized by Fourier transform infrared spectroscopy (FT-Nicolet model Protege 460; Nicolet Instrument Corp., Madison, Wis.), UV-visible spectroscopy (DU 7400 spectophotometer; Beckman Instruments, Fullerton, Calif.), mass spectrometry (Finnigan MAT 95 mass spectrometer, Madison, Wis.) and elemental analysis (Atlantic Microlab, Inc., Norcross, Ga.). These oxovanadium (IV) complexes have a square pyramidal geometry with the oxo ligand (O$^{2-}$) in the apical site. The peroxivanadates are stabilized with bidentate ligands which form a 5-membered ring with the vanadium atom. The choice of these three organic ligands (phenanthroline, bipyridyl, and acetophenone) was based on the reported fact that the cationic oxovanadium (IV) complex of phenanthroline is superior to cisplatin (cis-diamminedichloroplatinum[II]) with respect to antitumor activity (Sakurai et al., 1995, *Supra*), the structural similarity of bipyridyl ring to phenanthroline, as well as the neutral nature of acetophenone complex of oxovanadium (IV). Structural variations of the ligands included addition of bromo, chloro or methyl groups on the phenanthroline, bipyridyl or acetophenone rings.

Sperm Immobilization Assay (SIA)

To evaluate the spermicidal effects of complexes of oxovanadium (IV), VO(phen), VO(phen)$_2$, VO(Me$_2$—phen), VO(Me$_2$—phen)$_2$, VO(Cl—phen), VO(Cl—phen)$_2$], VO(bipy), VO(bipy)$_2$, VO(Me$_2$—bipy), VO(Me$_2$—bipy)$_2$, and VO(Br,OH—acph)$_2$, a highly motile fraction of pooled donor sperm (N=5) was prepared by discontinuous (90–45%). Percoll gradient (Conception Technologies, San Diego, Calif.) centrifugation and the "swim-up" method as described previously (Aitken et al., 1989, *Biol. Reprod.* 40:183–197). All donor specimens were obtained after informed consent and in compliance with the guidelines of the Hughes Institutional Review Board. Motile sperm ($\geq 10 \times 10^6$/ml) were suspended in 1 ml of Biggers, Whitten, and Whittingham's medium (BWW) containing 0.3% BSA (fraction V; Sigma Chemical Co., St. Louis, Mo.) in the presence and absence of serial 2-fold dilutions of test substance (250 µM–1.9 µM) in 0.25% dimethyl sulfoxide (DMSO). For each experiment, fresh stock solutions (100 mM) of vanadium compounds were prepared in DMSO. A corresponding volume of DMSO (0.25%) was added to control sperm suspension. After 3 hours of incubation at 37° C., the percentage of motile sperm was evaluated by computer-assisted sperm motion analysis (CASA) as described previously (Aitken et al., 1989, *Supra*). The percentages of motilities were compared with those of sham-treated control suspensions of motile sperm. The spermicidal activity of test compounds was expressed as the $EC_{50}$ values (the final concentration of the compound in medium that decreases the proportion of motile sperm by 50%).

To test the effect of duration of incubation on sperm immobilization in the presence of oxovanadium (IV) complexes, a motile fraction of sperm ($10^7$/ml) was incubated at 37° C. in 1 ml of BWW–0.3% BSA in the presence of 200 $\mu$M each of the complexes or 0.2% DMSO alone. At timed intervals (every 5 and 10 minutes) aliquots (4 $\mu$l) were transferred to two 20 $\mu$m Microcell (Conception Technologies) chambers, and sperm motility was assessed by CASA.

Sperm Kinematic Parameters

For CASA, 4 $\mu$l each of sperm suspension was loaded into two 20 $\mu$m Microcell chambers placed onto a counting chamber at 37° C. At least 5–8 fields per chamber were scanned for analysis using a Hamilton Thorne Integrated Visual Optical System (IVOS) version 10 instrument (Hamilton Thorne Research Inc., Danvers, Mass.). Each field was recorded for 30 seconds. The Hamilton Thorne computer calibrations were set at 30 frames at a frame rate of 30 images/seconds. Other settings were as follows: minimum contrast 8; minimum size 6; low-size gate, 1.0; high-size gate,2.9; low-intensity gate, 0.6; high-intensity gate, 1.4; phase-contrast illumination; low path velocity at 10 $\mu$m/seconds and threshold straightness at 80%; magnification factor, 1.95. The performance of the analyzer was periodically checked using the playback function.

The attributes of sperm kinematic parameters evaluated included number of motile (MOT) and progressively (PRG) motile sperm; curvilinear velocity (VCL; a measure of the total distance traveled by a given sperm during the acquisition divided by the time elapsed); average path velocity (VAP; the spatially averaged path that eliminates the wobble of the sperm head), straight-line velocity (VSL; the straight-line distance from beginning to end of track divided by time taken), beat-cross frequency (BCF; frequency of lateral head displacement), (ALH; the mean width of sperm head oscillation), and the derivatives, straightness (STR=VSL divided by VAP×100), linearity (LIN=VSL divided by VCL×100, departure of sperm track from a straight line). Data from each individual cell track were recorded and analyzed. At least 200 sperm were analyzed for each aliquot sampled.

Flow Cytometric Quantitation of Sperm Acrosome Reaction

In experiments designed to assess the comparative effects of oxovanadium (IV) complexes and N-9 on sperm acrosome reaction, motile fractions of sperm ($10^7$/ml) prepared from a single donor were incubated in 1 ml of BWW–0.3% BSA in the presence of 100 $\mu$M each of the vanadocene complexes, VO(phen), VO(phen)$_2$, VO(Me$_2$—phen), VO(Me$_2$—phen)$_2$, VO(Cl—phen), VO(Cl—phen)$_2$, VO(bipy), VO(bipy)$_2$, VO(Me$_2$—bipy), VO(Me$_2$—bipy)$_2$, and VO(Br,OH—acph)$_2$ in 0.1% DMSO, N-9, or DMSO (0.1%) alone at 37° C. After 3 hours, 5 $\mu$g/ml of purified, phycoerythrin (PE)-conjugated murine anti-CD46 monoclonal antibody (mAb; clone 122-2; Research Diagnostics, Flanders, N.J.) was added and the sperm suspensions incubated for an additional 30 minutes. The suspensions was washed in Tyrode's salt solution (Sigma) containing 1% BSA (1% TBSA) and the percentage of CD46-positive sperm were analyzed by flow cytometry using a FACS Vantage flow cytometer (Becton Dickinson, Mountain View, Calif.), as described previously (DeCruz et al., 1996, Biol Reprod. 54:1217–1228; DeCruz et al., 1992, Fertil. Seril., 58:633–636). Two separate experiments were performed to quantitate acrosomal loss following exposure of sperm to oxovanadium (IV) complexes.

Flow Cytometric Assays for Oxovanadium (IV) Complex-Induced Apoptosis

Three independent flow cytometric apoptotic assays were used to determine oxovanadium (IV)-mediated quantitative changes at the mitochondrial, surface membrane, and sperm nuclear compartments. These data are shown in FIGS. 4A–4F.

Assessment of Mitochondrial Transmembrane Potential ($\Delta\Psi$m) Using JC-1 Dye:

The loss of $\Delta\Psi$m, a early marker for apoptosis was quantitated by flow cytometry using the lipophilic cationic dye, 5,5',6,6'-tetrachloro 1,1',3,3'-tetraethylbenzimidazolecarbocyanine iodide (JC-1) as described in Cossarizza et al., 1993, BBRC 197:40–45. This dye accumulates in the mitochondrial matrix under the influence of the $\Delta\Psi$m. The molecule is able to selectively enter into mitochondria, the monomeric form emitting at 527 nm after excitation at 490 nm. However, depending on the membrane potential, JC-1is able to form J-aggregates that are associated with a large shift in emission (590 nm). The color of the dye changes reversibly from green to greenish orange at $\Delta\Psi$m becomes more polarized.

To quantitate changes in sperm $\Delta\Psi$m following oxovanadium (IV) complex exposure, highly motile fraction of sperm ($10^7$/ml) in duplicate aliquots, were incubated at 37° C. for 3 hours in BWW–0.3% BSA medium in the presence and absence of 100 $\mu$M each of the vanadocene complexes, VO(phen), VO(phen)$_2$, VO(Me$_2$—phen), VO(Me$_2$—phen)$_2$, VO(Cl—phen), VO(Cl—phen)$_2$, VO(bipy), VO(bipy)$_2$, VO(Me$_2$—bipy), VO(Me$_2$—bipy)$_2$, and VO(Br,OH—acph)$_2$. Following incubation, 10 $\mu$g/ml JC-1 (Molecular Probes, Eugene, Oreg.) was added from a stock solution in DMSO (1 mg/ml) to the sperm suspension and incubated for an additional 10 minutes. At the end of the incubation period, sperm were washed in Tyrode's salt solution (Sigma), resuspended in 200 $\mu$l, and analyzed by flow cytometry for JC-1-specific fluorescence. The excitation was at 488 nm; the emissions for green and red/orange fluorescence were 530 nm and 575 nm respectively. JC-1 monomer and aggregated fluorescence were simultaneously measured in oxovanadium (IV) complex-exposed and control sperm. The percentages of sperm positive for green, orange, and greenish orange were determined using the cutoff signals for JC-1 labeled motile sperm.

Assessment of Sperm Membrane Changes Using FITC Annexin V

In order to examine the expression of phosphatidyl serine on the sperm surface following oxovanadium (IV) complex exposure, surface binding of FITC-Annexin V was evaluated by flow cyotometry as described in Vermes et al., 1995, J. Immunol. Meth., 1984:39–51. One ml aliquots of highly motile sperm ($10^7$) in triplicate were incubated in BWW–0.3% BSA at 37° C. for 12 hours with and without 100 $\mu$M of each of the oxovanadium (IV) complexes VO(phen), VO(phen)$_2$, VO(Me$_2$—phen), VO(Me$_2$—phen)$_2$, VO(Cl—phen), VO(Cl—phen)$_2$, VO(bipy), VO(bipy)$_2$, VO(Me$_2$—bipy), VO(Me$_2$—bipy)$_2$, and VO(Br,OH—acph)$_2$ in 0.1% DMSO. After exposure to these complexes, sperm were washed with 1% Tyrode's salt solution containing 1% BSA (1% TBSA), and the pellets were resuspended in the same medium. The sperm suspension was reacted for 30 minutes at room temperature with 6 $\mu$g/ml of FITC-conjugated recombinant human Annexin V (Caltag Laboratories, San Francisco, Calif.). After two washes in Tyrode's salt solution, sperm were resuspended in 1% TBSA containing 1 $\mu$g/ml propidium iodide (PI) and analyzed for surface-bound Annexin V and PI-permeability by quantitative flow cytometry using an argon laser for excitation of fluorescence. Annexin V and PI binding were simultaneously measured in oxovanadium (IV) complex-exposed and control sperm as described previously (de Lamirande et al., 1993, Fertil Seril 59:1291–1295). The percentages of sperm positive for Annexin V and PI were determined using the cutoff signals for membrane-intact motile sperm. Two separate experiments were performed to assess the surface expression of phosphatidyl serine following exposure of sperm to oxovanadium (IV) complexes.

Assessment of DNA-Fragmentation Using In Situ DNA Nick-End Labeling by TUNEL Method A flow cytometric two-color terminal deoxynucleotidyl transferase (TdT) assay was employed to detect apoptotic sperm nuclei by TdT-mediated dUTP nick-end labeling (TUNEL, as described in Gavrieli et al., 1992, J. Cell Biol., 119:493–501). The comparative effect of the oxovanadium (IV) complexes, VO(phen), VO(phen)$_2$, VO(Me$_2$—phen), VO(Me$_2$—phen)$_2$, VO(Cl—phen), VO(Cl—phen)$_2$, VO(bipy), VO(bipy)$_2$, VO(Me$_2$—bipy), VO(Me$_2$—bipy)$_2$, and VO(Br,OH—acph)$_2$, to induce apoptosis was tested by incubating 1 ml duplicate aliquots of motile sperm (10$^7$/ml) in BWW–0.3% BSA at 37° C. for 24 hours with and without 100 $\mu$M each of the test compounds. Sperm were washed in phosphate-buffered saline (PBS)–1% BSA, fixed in 4% paraformaldehyde in PBS for 15 minutes. Following two washings in PBS, they were permeabilized with 0.1% Triton X-100 in 0.1% sodium citrate for 2 minutes on ice, and washed twice with PBS. New 3'-hydroxyl (3'—OH) end labeling of fragmented sperm nuclear DNA was performed using TdT and detected by fluorescein (FITC)-conjugated uridine triphosphate (dUTP) according to the manufacturer's recommendations (Boehringer-Mannheim, Indianapolis, Ind.). Sperm aliquots incubated without TdT enzyme served as a negative control. Nonapoptotic sperm do not incorporate significant amounts of dUTP due to lack of exposed 3'—OH ends, and consequently have much less fluorescence compared to apoptotic cells which have an abundance of 3'—OH ends. Oxovanadium (IV)-induced apopotosis of sperm was shown by an increase in the number of cells staining with FITC- dUTP (M2 gates). The M1 and M2 gates were used to demarcate non-apoptotic and apoptotic PI-counterstained sperm populations, respectively. Two separate experiments were performed to assess dUTP incorporation following exposure of sperm to oxovanadium (IV) complexes.

Confocal Laser Scanning Microscopy

Confocal microscopy of TUNEL-positive and control sperm was performed using a BioRad MRC 1024 Laser Scanning Confocal Microscope equipped with an argon-ion laser (excitation at 488 nm and emission at 540 nm) and mounted on a Nikon Eclipse 600 series upright microscope. Confocal images were obtained using a Nikon×100 (NA 1.4) numerical aperture objective and Kalman collection filter. Digitized images were saved on a Jaz disk (Iomega Corp., Roy, Utah) and processed with the Adobe Photoshop software (Adobe Systems, Mountain View, Calif.). Final images were printed using a Fuji Pictography 3000 (Fugi Photo Film Co., Tokyo, Japan) color printer.

Statistical Analysis

Results for the various numerical sperm functional parameters are presented as mean±standard deviation (SD) values. Comparison between oxovanadium (IV) complex-treated and control sperm relative to sperm motility parameters and apoptosis were performed using paired, two-tailed Student's T-test. A p value of <0.05 was considered significant. Non-linear regression analysis was used to find the EC$_{50}$ values (i.e. concentrations of compound that result in 50% sperm motility loss) from the concentration effect curve using GraphPad Prism software (San Diego, Calif.).

Results

Oxovanadium (IV) Complexes of 1,10-Phenanthroline, 2,2'-Bipyridyl and 5'-Bromo-2'-Hydroxyacetophenone and Derivatives Demonstrated Spermicidal Activity Oxovanadium (IV) complexes: phenanthroline (phen)-linked [VO(phen), VO(phen)$_2$, VO(Me$_2$—phen), VO(Me$_2$—phen)$_2$, VO(Cl—phen), and VO(Cl—phen)$_2$], bipyridyl (bipy)-linked [VO(bipy), VO(Me$_2$—bipy), and VO(Me$_2$—bipy)$_2$]via the nitrogen-metal bond, and acetophenone (acph)-linked [VO(Br,OH—acph)$_2$]via oxygen-metal bond, were synthesized and tested them for spermicidal activity using CASA. These complexes were tested side-by-side and at 8 different concentrations ranging from 1.9 $\mu$M to 250 $\mu$M.

Figure 2:
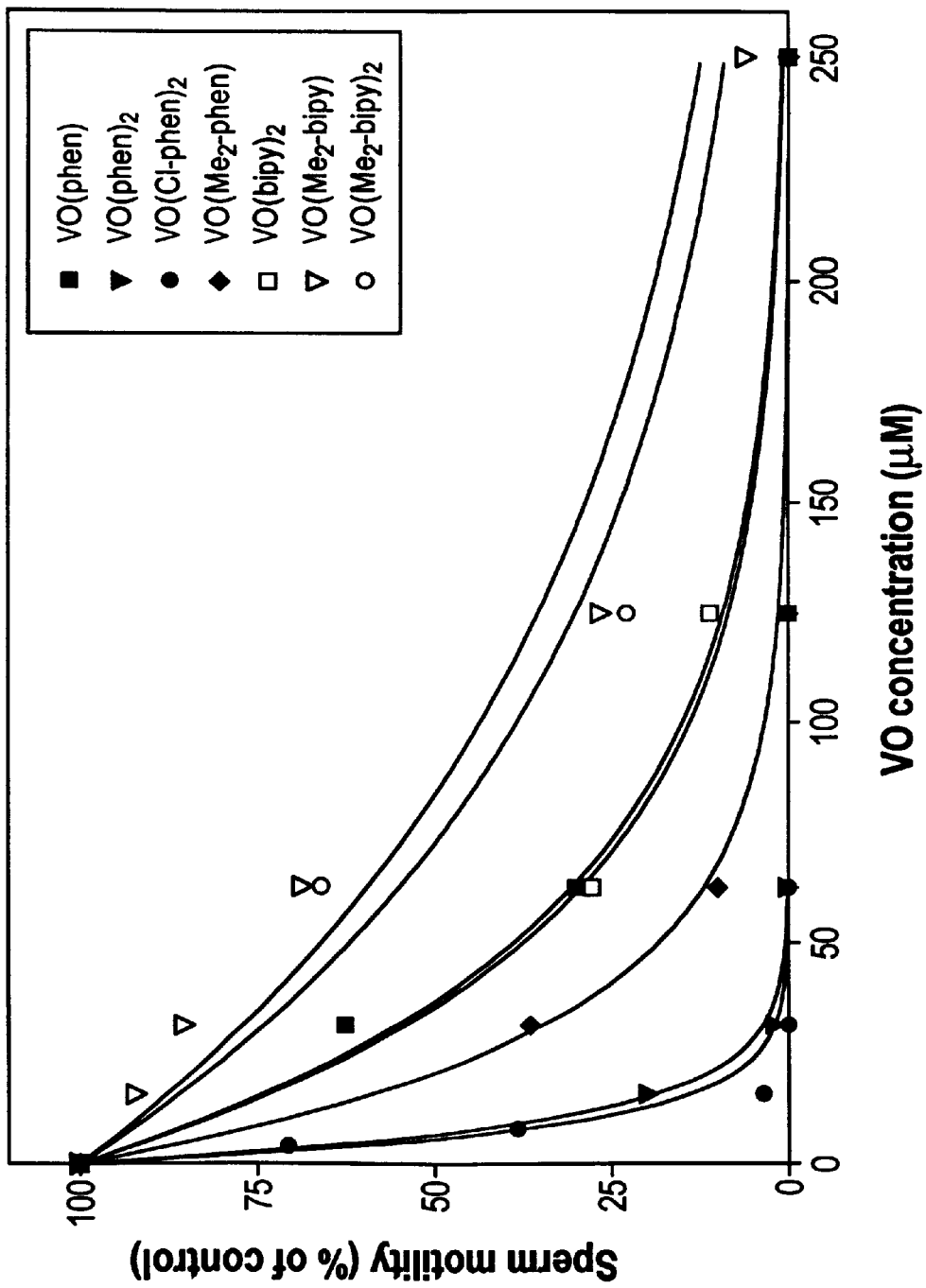
FIG. 2 is a graph showing spermicidal activity (loss of sperm mobility) after treatment with the spermicidal oxovanadium (IV) complexes of the invention.

All of the tested oxovanadium complexes coordinated as ligands to the central vanadium (IV) ion induced concentration-dependent inhibition of sperm motility assessed after a 3-hour incubation in BWW–0.3% BSA medium. However, marked differences were noted in their potency. FIG. 2 shows the concentration-response curves of spermicidal effects (loss of sperm motility) of representative oxovanadium (IV) complexes, VO(phen), VO(phen)$_2$, VO(Cl—phen)$_2$, VO(Me$_2$—phen), VO(bipy)$_2$, VO(Me$_2$—bipy), and VO(Me$_2$—bipy)$_2$. Highly motile fractions of sperm were incubated for 3 hours with increasing two-fold concentrations (1.9–250 $\mu$M) of VO-complexes or DMSO alone in the assay medium. The percentage of motile sperm was evaluated by CASA. Each point represents the mean of from 2 to 4 independent experiments.

Among the phenanthroline-linked cationic complexes, bis-1,10-phenanthroline complex, CO(phen)$_2$ and its 5-chloro derivative, VO(Cl—phen)$_2$, were the most potent, with EC$_{50}$ values of 6.5 $\mu$M and 5.5 $\mu$M, respectively (see FIG. 2 and Table 1).

Table 1 shows comparative spermicidal activity analyzed by CASA and acrosomal loss analyzed by the flow cytometric anti-CD46 mAb binding assay following exposure of sperm to oxovanadium(IV) complexes containing either mono and bis 1,10-phenanthroline, 2,2'-bipyidyl or 5'-bromo-2'-hydroxyacetophenone and derivatives.

TABLE 1

| Treatment | EC$_{50}$ ($\mu$M)[a,b] | Anti-CD46 positive sperm (%)[a,c] |
|---|---|---|
| DMSO control | NA | 5.2 ± 0.7 |
| VO(phen) | 37 | 9.7 ± 0.7 |
| VO(phen)$_2$ | 6.5 | 9.9 ± 3.4 |
| VO(Me$_2$-phen) | 20.5 | 14.0 ± 2.5[d] |
| VO(Me$_2$-phen)$_2$ | 47.9 | 11.7 ± 1.1[d] |
| VO(Cl-phen) | 39.1 | 11.2 ± 0.9 |
| VO(Cl-phen)$_2$ | 5.5 | 21.5 ± 0.5[d] |
| VO(bipy) | 118 | 6.1 ± 1.2 |
| VO(bipy)$_2$ | 35.3 | 4.7 ± 0.3 |
| VO(Me$_2$-bipy) | 83 | 6.4 ± 0.8 |
| VO(Me$_2$-bipy)$_2$ | 72.5 | 3.2 ± 0.6 |
| VO(Br,OH-acph)$_2$ | 13.4 | 24.3 ± 0.6[d] |
| N-9 | 78.5 | 86 ± 2[d] |

[a]Mean of two experiments.
[b]Stock solutions (100 mM) in DMSO were tested in serial 2-fold dilutions from 250 $\mu$M to 1.9 $\mu$M.
[c]Tested at 100 $\mu$M.
[d]p < 0.05 compared with DMSO control.

The 5-bromo derivative of bis-2'-hydroxyacetophenone, a neutral complex, also demonstrated potent spermidical activity, with an EC$_{50}$ value of 13.4 $\mu$M. Among the bipyridyl-linked cationic complexes, the bis-2,2'-bipyridyl complex, VO(bipy)$_2$, and its 4,7-dimethyl derivative, VO(Me$_2$—bipy)$_2$ were the most active, with EC$_{50}$ values of 35.3 $\mu$M and 72.5 $\mu$M, respectively. The mono-2,2'-bipyridal complex, VO(bipy), was the least active (EC$_{50}$=118 $\mu$M). Thus, the spermicidal activity of oxovanadium (IV) complexes was strongly dependent on the coordinated heteroligands.

Oxovanadium (IV) complexes having a bidentate ligand which formed a 5-membered ring with the vanadium (IV) atom, a "butterfly structure," demonstrated superior spermicidal activity when compared with the activity of monodentate ligands (see FIG. 1, Table 2).

In Table 2, the apoptosis-inducing property of spermicidal oxovanadium (IV) complexes containing mono and bus 1,10-phenanthroline, 2,2'-bipyridyl and 5'-bromo-2'-hydroxyacetophenone and derivatives is shown.

TABLE 2

| Treatment | JC-1 aggregate-positive sperm (%)[a] | Annexin V positive sperm (%)[a] | TUNEL positive sperm (%)[a] |
|---|---|---|---|
| DMSO control | 92 ± 3 | 7 ± 3 | 9 ± 1 |
| VO(phen) | 35 ± 12[c] | 97 ± 1[c] | 98 ± 1[c] |
| VO(phen)$_2$ | 25 ± 1[c] | 98 ± 1[c] | 98 ± 1[c] |
| VO(Me$_2$-phen) | 38 ± 2[c] | 96 ± 3[c] | 97 ± 1[c] |
| VO(Me$_2$-phen)$_2$ | 63 ± 2[c] | 17 ± 1 | 94 ± 1[c] |
| VO(Cl-phen) | 39 ± 4[c] | 90 ± 2[c] | 95 ± 1[c] |
| VO(Cl-phen)$_2$ | 35 ± 1[c] | 99 ± 1[c] | 97 ± 1[c] |
| VO(bipy) | 95 ± 1 | 36 ± 8[c] | 43 ± 16[c] |
| VO(bipy)$_2$ | 94 ± 1 | 26 ± 1 | 40 ± 22 |
| VO(Me$_2$-bipy) | 88 ± 5 | 47 ± 16[c] | 45 ± 10[c] |
| VO(Me$_2$-bipy)$_2$ | 62 ± 5[c] | 78 ± 7[c] | 63 ± 22[c] |
| VO(Br,OH-acph)$_2$ | 83 ± 3 | 95 ± 1[c] | 98 ± 1[c] |

[a]Motile sperm were incubated at 37° C. for 3, 12, and 24 hours respectively, in either control medium, or in medium supplemented with 100 $\mu$M each of the oxovanadium (IV) complexes, and stained respectively with either JC-1, FITC-Annexin V or with FITC-dUTP, and analyzed by flow cytometry.
[b]Mean of two separate experiments.
[c]p < 0.05 compared with DMSO control.

The concentrations of oxovanadium (IV) complexes with mono and bidentate ancillary ligands, VO(phen), VO(phen)$_2$, VO(Me$_2$—phen), VO(Me$_2$—phen)$_2$, VO(Cl—phen), VO(Cl—phen)$_2$, VO(bipy), VO(bipy)$_2$, VO(Me$_2$—bipy), VO(Me$_2$—bipy)$_2$ and VO(Br, OH—acph)$_2$ that inhibited sperm motility by 50% (EC$_{50}$ values) calculated from concentration-response curve were 37 $\mu$M, 6.5 $\mu$M, 20.5 $\mu$M, 47.9 $\mu$M, 39.1 $\mu$M, 5.5 $\mu$M, 118 $\mu$M, 35.3 $\mu$M, 83 $\mu$M, 72.5 $\mu$M, and 13.4 $\mu$M, respectively (Table 1). These marked differences (21-fold) in potency of the spermicidal activity elicited by three ancillary heteroligands and their derivatives suggest that spermicidal potency of oxovanadium (IV)-complexes is modulated by the coordinated ligands. The spermicidal activity of the most potent oxovanadium (IV) complex, VO(Cl—phen)$_2$, was 14-fold more potent than that of the commercial detergent-based spermicide, N-9 (78.5 $\mu$M), when tested under identical experimental conditions.

Also, in comparison to N-9, the spermicidal activity of oxovanadium (IV) complexes was not associated with a concomitant loss of acrosomal membrane as quantitated by the flow cytometric anti-Cd46 mAb binding assay using unfixed sperm suspension. Despite complete sperm motility loss quantitated after a 3 hour incubation period, 76% to 97% of the treated sperm remained anti-CD46 negative (acrosome-intact) (Table 1). The most potent oxovanadium (IV) complexes, VO(Cl—phen)$_2$ and VO(Br,OH—acph)$_2$ after a 3 hour incubation period induced a 4- to 5-fold (21.5% ±0.5% and 24.3% ±0.6% respectively, p<0.05) increase in acrosome reactions over control (5.2% ±0.7%), however, complete sperm motility loss with these complexes was achieved within 2 and 10 minutes of exposure. Thus, the spermicidal activity of oxovanadium (IV) complexes was not concomitantly associated with disruption of sperm membranes.

Kinetics of Sperm Immobilization by Oxovanadium (IV) Complexes was Variable

Interestingly, the kinetics of sperm immobilization by the oxovanadium (IV) complexes was variable. The corresponding times required for 50% motility loss of progressively motile sperm exposed to these complexes ranged from <1 minute to >60 minutes. Sperm immobilization by the neutral complex, VO(Br,OH—acph)$_2$ was the fastest followed by VO(Cl—phen)$_2$ with T$_{1/2}$ values of 38 seconds and 7.3 minutes respectively. The other cationic oxovanadium (IV) complexes showed a lag period of 30–60 minutes to bring about >50% sperm motility loss. By comparison, sperm motility in control samples remained stable during the 3-hour monitoring period.

Oxovanadium (IV) Complexes Affect Sperm Kinematics

The observed concentration- and time-dependent decrease in sperm motility after exposure to oxovanadium (IV) complexes were associated with significant changes in the centroid-derived movement characteristics of the surviving sperm, particularly with respect to the track speed (VCL), straight line velocity (VSL), and path velocity (VAP).

Figure 3A:
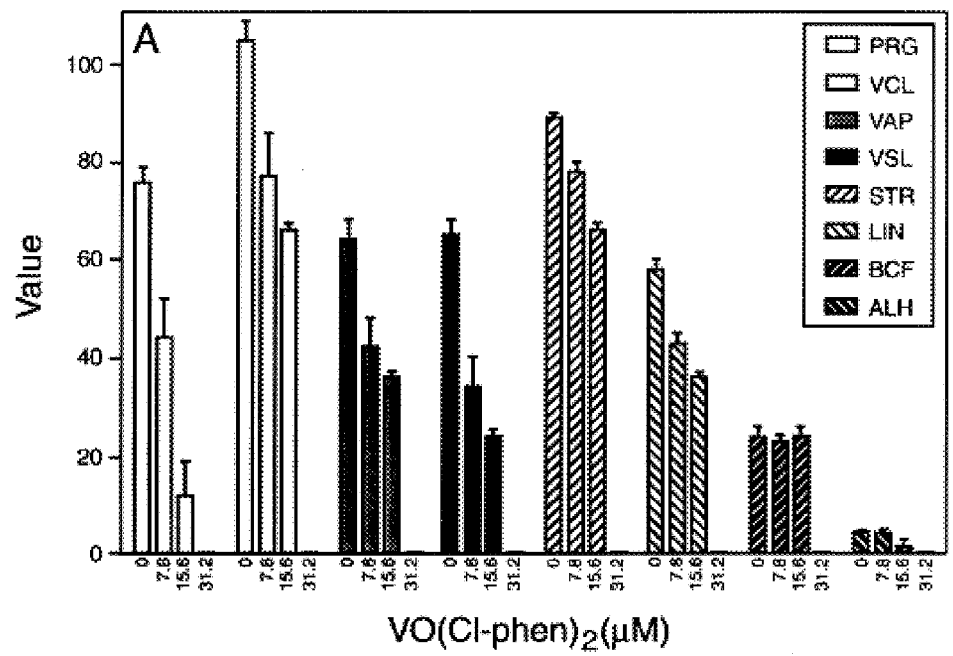
FIGS. 3A and 3B are bar graphs showing the inhibition of sperm motion parameters measured by CASA after treatment with VO (Cl-phen)$_2$.
Figure 3B:
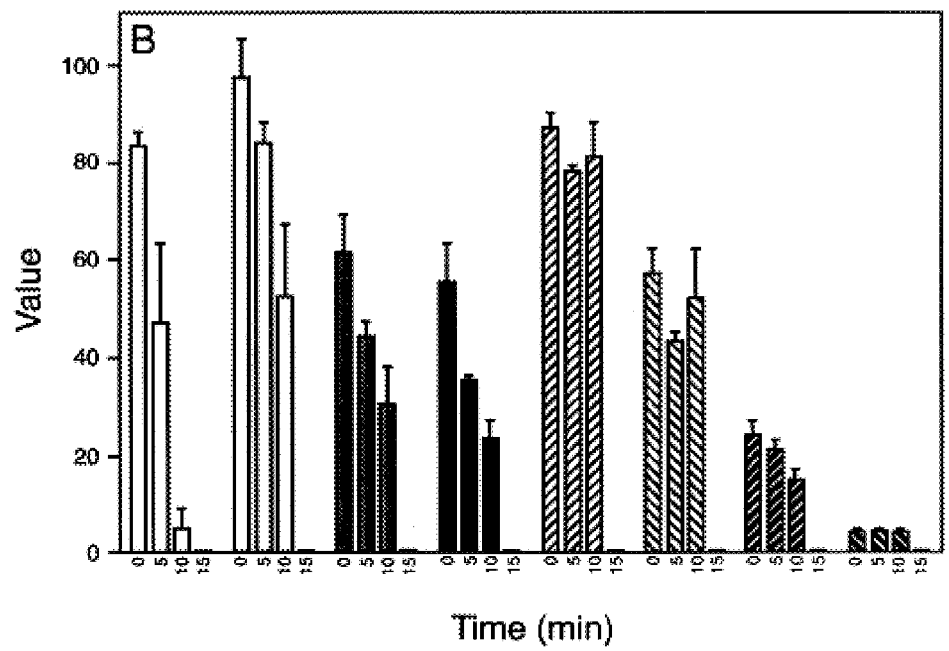

The representative sperm kinematic parameters observed for VO(Cl—phen)$_2$ versus concentration and time are shown FIGS. 3A and 3B respectively. The effect of bis 5-chloro-1,10-phenanthroline oxovanadium (IV) sulfate, VO(Cl—phen)$_2$, on sperm motion parameters analyzed by CASA. In FIG. 3A, the concentration-dependent inhibition of sperm motility parameters is shown. Motile fractions of sperm were incubated in assay medium in the presence of three increasing concentrations of VO(Cl—phen)$_2$ (0, 7.8, 15.6, and 31.2 $\mu$M) for 3 hours at 37° C., and the centroid-derived motility characteristics were determined using the Hamilton-Thorne-IVOS version 10 CASA. In FIG. 3B, the time-dependent effect of VO-complexes on sperm kinematics is shown. Motile fractions of sperm were incubated for 5, 10, and 15 minutes in assay medium in the presence of 200 $\mu$M of VO(Cl—phen)$_2$, and the motility characteristics were determined by CASA as described under "Materials and Methods," above. The sperm motion parameters were (left to right): MOT=motility (%); VCL=curvilinear velocity ($\mu$m/s); VSL=straight line velocity ($\mu$m/s);l VAP=average path velocity ($\mu$m/s); STR=straightness, VSL/VAP (%); LIN=linearity, VSL/VCL (%); BCF=beat/cross frequency (Hz); and ALH=amplitude of lateral head displacement (($\mu$m). Values are mean±SD of two representative experiments. Significant difference (P<0.05) between control and VO(Cl—phen)$_2$-treated sperm: progressive motility, VCL, VAP, and VSL.

The decreases in VCL, VSL, and VAP were similar in magnitude with increasing concentrations of VO(Cl—phen)$_2$ or exposure time. However, the linearity (LIN) of the sperm tracks and the straightness (STR) of the swimming pattern were affected only with increasing concentration of the drug. The beat-cross frequency (BCF) and the amplitude of lateral sperm head displacement (ALH) were relatively uniform as the proportion of motile sperm declined with increasing concentration (0–15.6 $\mu$M) or exposure time (0–10 minutes). By contrast, the sperm motion parameters of control sperm showed insignificant changes during the 3-hour exposure.

Example 2

Oxovanadium (IV) Complexes of 1,10-Phenanthroline, 1,2'-Bipyridyl, and 5'-Bromo-2'-Hydroxyacetophenone and Derivatives Induced Apoptosis The oxovanadium (IV) complexes with phenanthroline, bipyridyl and acetophenone as ancillary ligands were analyzed for their ability to induce apoptosis in human sperm. Three independent apoptosis assays were used to quantitatively assess changes at the mitochondrial, surface membrane, and nuclear level. Analysis by flow cytometry of mitochondrial membrane potential changes occurring during apoptosis were analyzed with a $\Delta\Psi m$ indicator, JC-1, a carbocyanine cationic dye by following fluorescence associated with the uptake of JC-1 to evaluate $\Delta\Psi m$ modifications as described in Smiley et al., 1991, (*PNAS USA* 88:371–3675). Motile sperm exhibit intense green and red fluorescence of JC-1, as shown in the flow cytometric quantitation, FIG. 4A.

Motile sperm were incubated at 37° C. in either control medium (0.1% DMSO) or medium supplemented with 100 $\mu M$ of a representative oxovanadium (IV) complex, VO(Cl—phen)$_2$. The apoptosis-inducing ability of VO(Cl—phen)$_2$ (FIGS. 4B, 4D, and 4F) in comparison with medium control (FIGS. 4A, 4C, and 4E) was tested by three flow cytometric assays that quantitatively assess changes at the mitochondrial membrane potential based on JC-1 staining (FIGS. 4A and 4B); surface plasma membrane based on FITC-Annexin V-staining (FIGS. 4C and 4D), and sperm nuclear compartment based on FITC-dUTP nick-end labeling of fragmented DNA (FIGS. 4E and 4F) after 3, 12, and 24 hours respectively. Note the marked reduction in JC-1 red fluorescence (aggregates) labeling with no reduction in green emission (monomers). In FIGS. 4C–4F, sperm nuclei were counter-stained with propidium iodide.

It can be seen that a 3 hour treatment with oxovanadium (IV) complex, VO(Cl—phen)$_2$, resulted in an extinction of the red fluorescence (FIG. 4B) indicating that alteration occurs following VO(CL—phen)$_2$ treatment. A 3 hour pre-treatment of sperm with 7 of the oxovanadium (IV) complexes resulted in variable decrease of $\Delta\Psi m$-related fluorescence observed as 31% to 73% reduction (p<0.05) in JC-1 aggregate (orange/green) fluorescence without concomitant reduction in JC-1 monomer (green) fluorescence (Table 2). By contrast, >90% of control sperm were positive for orange/red fluorescence. The most potent spermicidal agents, VO(Cl—phen)$_2$ and VO(phen)$_2$ induced the maximum shift. Therefore, $\Delta\Psi m$ modifications, evaluated by the uptake of cationic lipophilic dye, are detected early in the process of apoptosis induced by oxovanadium (IV) complexes.

Figure 4A:
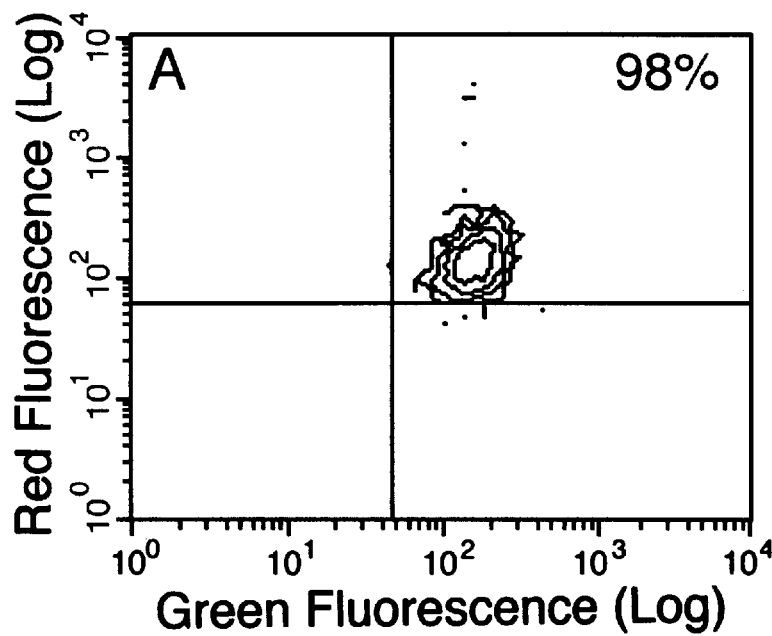
FIGS. 4A–4F are scans demonstrating VO-complex induced apoptosis in treated sperm analyzed by flow cytomeric quantitation.
Figure 4B:
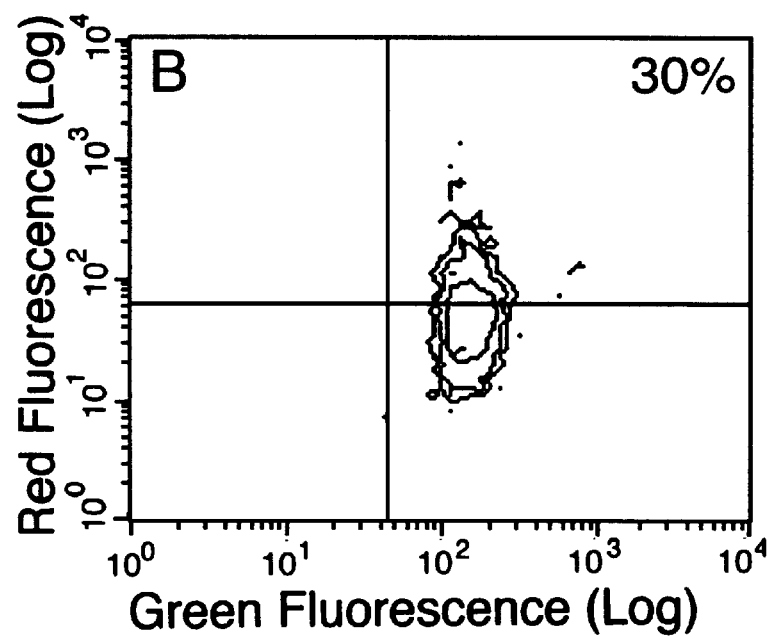
Figure 4C:
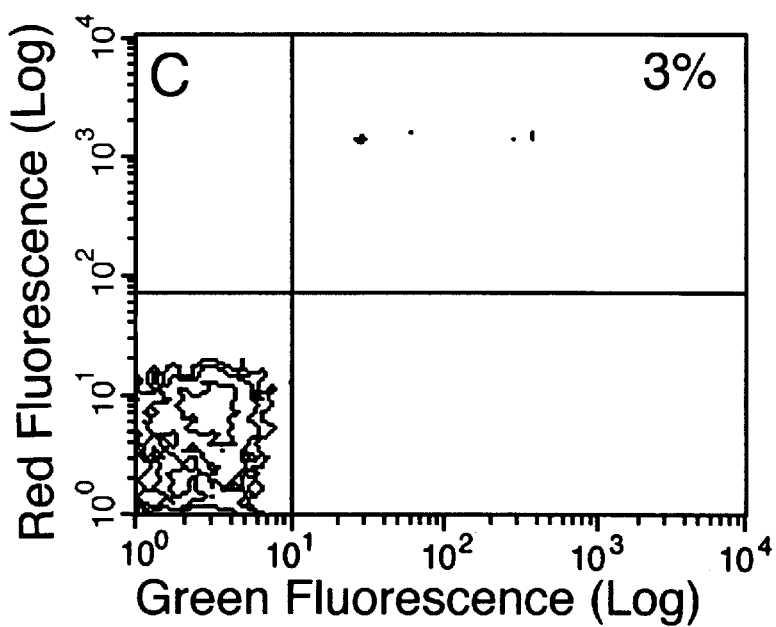
Figure 4D:
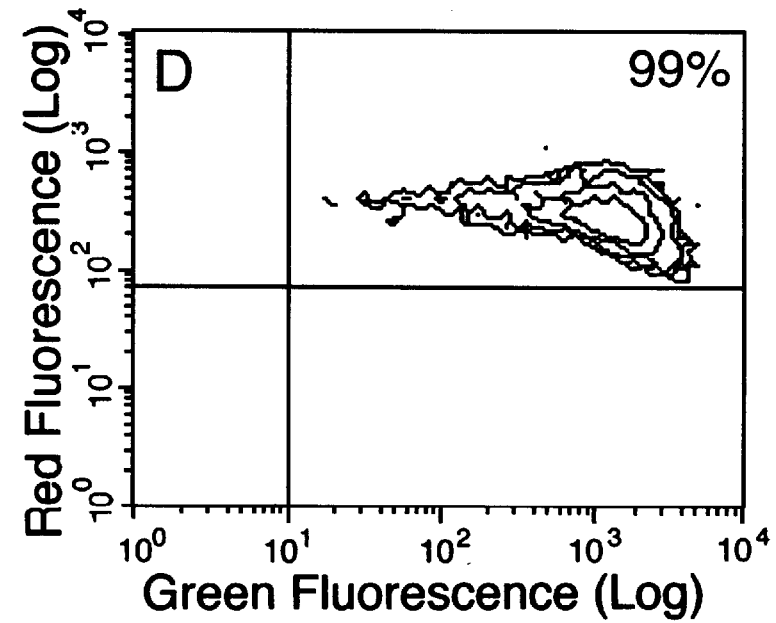

Changes in the plasma membrane of the cell surface also appear early in cells undergoing apoptosis. In apoptotic cells, the membrane phospholipid phosphatidyl serine is translocated from the inner to the outer leaflet of the plasma membrane, thereby exposing phosphatidyl serine to the external cellular environment. Annexin V binds to phosphatidyl serine residues which are exposed on the surface of cells undergoing apoptosis. The apoptosis-dependent surface binding of FITC-labeled recombinant human Annexin V with 10 of the 11 tested oxovanadium (IV) complex-treated sperm showed a dramatic increase in binding of Annexin V to sperm membrane (Table 2). After 12 hours of incubation, 26% to 99% (p<0.05) of the treated sperm were apoptotic. Control sperm exhibited minimal fluorescence (FIG. 4C). By contrast, 99% of VO(Cl—phen)$_2$-treated sperm were positive for FITC-Annexin V (FIG. 4D) indicating that surface membrane alteration occurs following prolonged exposure to oxovanadium (IV) complexes. Control sperm treated with 0.1% of DMSO alone showed only 7±3% Annexin V positivity at 12 h. The most potent spermicidal complexes, VO(Cl—phen)$_2$, and VO(phen)$_2$, also induced maximum Annexin V positivity.

Figure 4E:
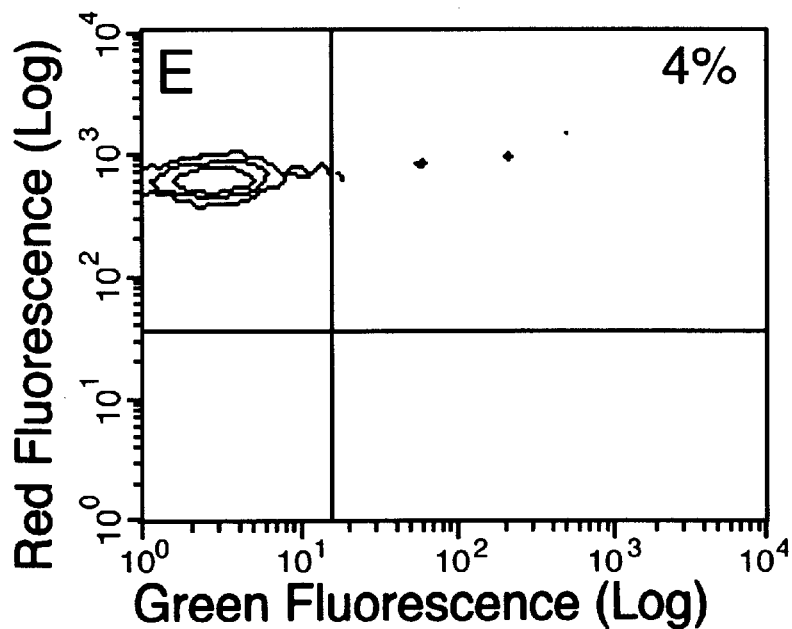
Figure 4F:
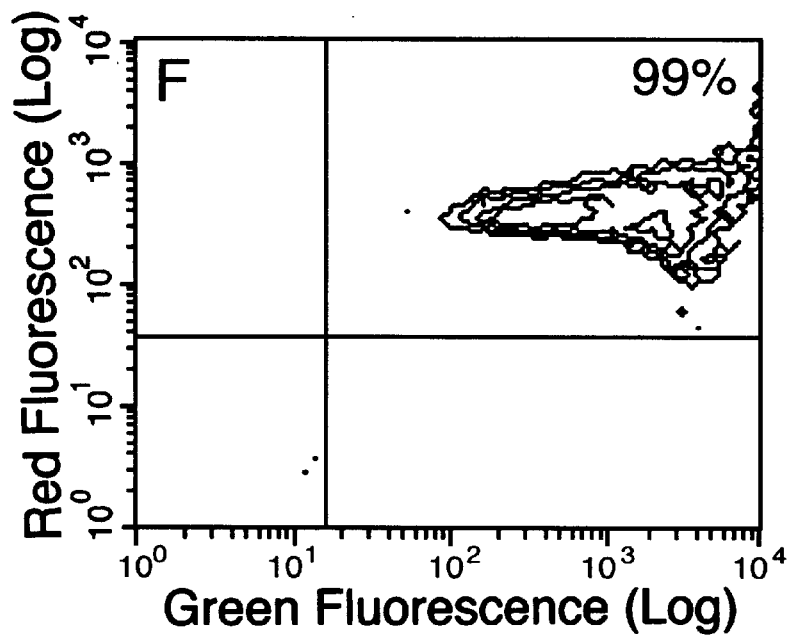

Next, TdT-mediated labeling of exposed 3'-OH termini for nuclear DNA with FITC-conjugated dUTP by the in situ TUNEL method was employed to demonstrate that oxovanadium (IV) complexes induce apoptosis in the sperm nuclear compartment. FIGS. 4E and 4F depicts the two-color cytometric contour plots of sperm nuclei of control sperm (E) treated with 0.1% DMSO, and test sperm (F) treated with 100 $\mu M$ of VO(Cl—phen)$_2$ in 0.1% DMSO after staining with FITC-dUTP and counterstaining with PI. Greater than 97% of VO(Cl—phen)$_2$ treated sperm became apoptotic (TUNEL-positive) after a 24 hour of incubation. A 24 hour exposure of sperm with any one of the 11 oxovanadium (IV) complexes evaluated resulted in marked increase of TUNEL-positive cells observed as 43% to 98% (p<0.05) increase in FITC-dUTP fluorescence (Table 2). By contrast, <10% of control sperm treated with 0.1% DMSO alone showed apoptotic nuclei after a 24 hour of incubation. The percentages of apoptotic sperm quantitated by the flow cytometric assays correlated well with the potency ($EC_{50}$ values) of these oxovanadium (IV) complexes in sperm immobilization assays. Confocal images of TUNEL-positive sperm clearly indicated that the fluorescence was localized to sperm nuclear region.

Figure 5A:
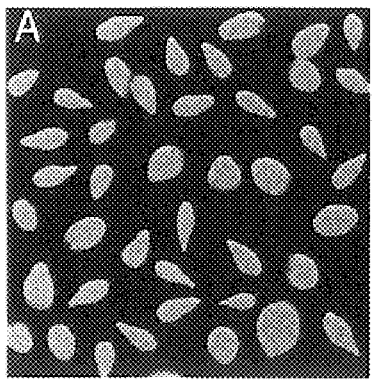
FIGS. 5A–5C are confocal laser scanning microscopy images of sperm nucleic undergoing apoptosis following treatment with VO(Cl-phen)$_2$.
Figure 5B:
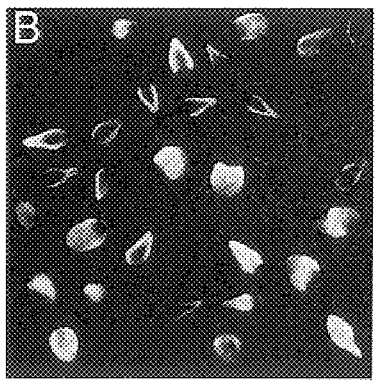
Figure 5C:
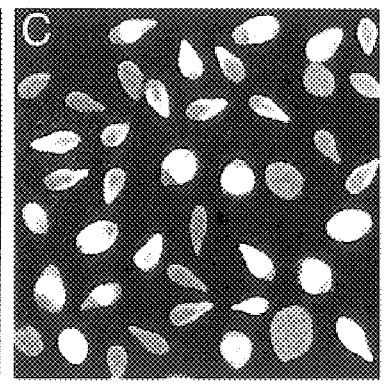

FIGS. 5A–5C show confocal microscopy images of sperm nuclei treated with 100 $\mu M$ VO(Cl—phen)$_2$ in 0.1% DMSO after incubation with TdT and FITC-dUTP with (FIGS. 5A and 5C) and without (FIG. 5B) PI counterstaining. Nuclei of VO(CL—phen)$_2$-treated sperm showed dual fluorescence (FIG. 5C) consistent with apoptosis.

Confocal laser scanning microscopy images of sperm nuclei undergoing apoptosis following treatment with a oxovanadium (IV) complex, VO(Cl—phen)$_2$. Motile sperm were incubated for 24 hours in medium supplemented with 100 $\mu M$ VO(Cl—phen)$_2$, fixed, permeabilized, and visualized for DNA degradation in a TUNEL assay using TdT and FITC-dUTP. FIG. 5A shows sperm nuclei counterstained with PI (red color). FIG. 5 shows sperm nuclei visualized for dUTP incorporation using FITC-dUTP (green). FIG. 5C shows nuclei of VO(Cl—phen)$_2$-treated sperm visualized for dual fluorescence. Apoptotic nuclei appear yellow due to superimposed labels. Original magnification ×1000.

DISCUSSION

The above described results provide unprecedented evidence that oxovanadium (IV) complexes with 1,10-phenanthroline, 2,2'-bipyridyl, or 5'-bromo-2'-hydroxyacetophenone and their derivatives linked to vanadium via nitrogen or oxygen bond have potent spermicidal activity against human sperm. The order of spermicidal efficacy for oxovanadium (IV) complexes synthesized and evaluated was: VO(Cl-phen)$_2$>VO(phen)$_2$>VO(Br,OH-acph)$_2$>VO(Me$_2$-phen)>VO(bipy)$_2$>VO(phen)>VO(Cl-phen)>VO(Me$_2$-phen)$_2$>VO(Me$_2$-bipy)$_2$>VO(Me$_2$-bipy). Thus, despite the structural similarities of phenanthroline and bipyridyl rings, the phenanthroline complexes of oxovanadium (IV), particularly the bis-phenanthroline complex, VO(Cl-phen)$_2$, were the most active and the mono bipyridal complex, VO(bipy), being the least active. In general, the oxovanadium (IV) complexes stabilized by bidentate ligands which formed a 5-membered ring with vanadium (IV) atom were 3- to 7-fold more potent when compared with monodentate complexes.

The kinetics of sperm immobilization by these oxovanadium (IV) complexes attached to various ancillary ligands was dependent on their net charge. Comparative structure-activity relationship analyses of vanadocenes (U.S. Ser. No. 09/008,989) and the oxovanadium (IV) complexes of the invention clearly demonstrated that the spermicidal properties of the organovanadium (IV) complexes and oxovanadium (IV) complexes was dependent upon the central vanadium (IV) ion within these complexes, the various ancillary ligands linked by carbon, nitrogen, or oxygen bonds to central vanadium (IV) ion significantly contributed either to fine tuning of the spermicidal potency or enhancing the stability of these complexes in aqueous solution. In addition, similar to our earlier findings with neutral complexes of vanadocenes, the neutral complex of oxovanadium (IV), VO(Br,OH-acph)$_2$ rapidly inactivated sperm in comparison to the cationic oxovanadium (IV) complexes or cationic vanadocenes which required a lag period of several minutes.

Therefore, it appears from our study that despite the tetrahedral geometry of the "bent-sandwich" structures of vanadocenes and the square pyramidal geometry or the "butterfly" structures of oxovanadium (IV) complexes, the rapidity of vanadium (IV)-dependent spermicidal activity was dependent on neutral charge of these complexes. The fact that the neutral complex of oxovanadium (IV), VO(Br, OH-acph)$_2$ induced both a potent and rapid sperm motility loss suggests that this complex of oxovanadium (IV) is rapidly transported across the sperm cell membranes. Because of its rapidity (sperm immobilization $T_{1/2}$=38 seconds) and potency, VO(Br,OH-acph)$_2$ provides a useful contraceptive agent.

The mechanism of sperm motility loss induced by oxovanadium (IV) complexes is unknown. Both the vanadocenes and oxovanadium (IV) complexes of vanadium (IV) have antitumor activity (Sakurai et al., 1995, *BBRC*, 206:133–137). The antitumor effects of vanadium (IV) complexes are thought to be due to their reaction with $H_2O_2$ forming hydroxyl radical in a Fenton-like reaction. In particular, the oxovanadium (IV) complex, following dissociation of phenanthroline rings leads to the formation of peroxocompounds which in the presence of $H_2O_2$ generates hydroxyl radicals. In support of this hypothesis is the observation that vanadyl-phen complex induces hydroxyl radical-dependent DNA cleavage in the presence of $H_2O_2$. The vanadyl complex, [VO(phen)(H$_2$O$_2$)$_2$]$_2^+$ has high antitumor activity toward human nasopharyngeal carcinoma. Hydrogen peroxide is formed in cells by dismutation of superoxide anions which are generated in various systems such as xanthine-oxidase, NADPH oxidase and NADH-dependent cytochrome P-450 and neutrophils. Thus, $H_2O_2$ is thought to react with oxovanadium (IV)-bound to DNA to generate ROS resulting in cleavage of DNA. It is likely that oxovanadium (IV)-induced sperm motility loss and apoptosis are mediated primarily by the ability to these complexes to induce ROS-mediated damage to sperm. In sperm, an NADPH-dependent superoxide generating system has been demonstrated (Kessopoulou et al, 1992, *J. Reprod. Fert* 94:463–470). In addition, the ability of $H_2O_2$ generating *Lactobacillus acidophilus* which is present in the vaginas of most normal women has the ability to further potentiate the spermicidal activity of intravaginally applied oxovanadium (IV) complex. This is in contrast to the commercial vaginal detergent spermicide, N-9, which is selectively toxic to Lactobacilli. Furthermore, unlike N-9, the spermicidal activity of the inorganic coordination complexes of vanadium (IV) was not concomitantly associated with membrane disruption.

The irreversible nature of the spermicidal activity of oxovanadium (IV) complexes is likely due to their ability to induce apoptosis. Three independent methods were used to quantitatively assess apoptotic changes in the mitochondria, surface membrane, and nuclear compartment. Mitochondria are the primary targets for apoptosis and alterations in mitochondrial structure and function are early events of apoptotic cell death. These studies demonstrated that spermicidal oxovanadium (IV) complexes induced depolarization of sperm mitochondria, an early marker for apoptotic cell death. Prolonged exposure of sperm to these spermicidal complexes also resulted in increased FITC-Annexin V binding to sperm surface due to membrane changes during apoptosis, as well as increased dUTP incorporation in the nuclei of treated sperm. Since vanadium (IV) compounds by themselves do not cleave DNA, the dramatic uptake of dUTP incorporation observed in our study appears to be due to the cleavage of the DNA polymer by the cytotoxic effects of reactive oxygen species-mediated effects of oxovanadium (IV) complexes. The fact that human sperm are exquisitely sensitive to oxidative stress, and the ability of vanadium (IV)-containing inorganic coordination complexes to potentiate these effects would make these oxovanadium (IV) complexes as a new class of gentle contraceptive agents.

The specification includes many references to patents and published literature, each of which is hereby incorporated by reference, for all purposes, as if fully set out herein.

We claim:

1. A method of inhibiting motility of sperm comprising contacting sperm with an organometallic oxovanadium IV complex comprising at least one substituted or unsubstituted ligand that is a 1,10 phenanthroline; a bridged or unbridged 2,2' bipyridyl; a 2'-hydroxyacetophenone; or a 3-hydroxypropenal.

2. The method of claim 1, wherein said complex comprises oxovanadium (IV) complexed with at least one bidentate ligand.

3. The method of claim 1, wherein said complex has the formula:

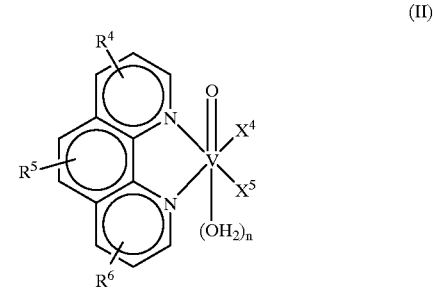

(II)

where $R^4$, $R^5$ and $R^6$ are the same or different and are each independently: H, lower alkyl, halogen, lower alkoxy, halogenated alkyl, cyano, carboalkoxy or nitro; $X^4$ and $X^5$ are the same or different and are each independently: monodentate or bidentate ligands; and n is 0 or 1.

4. The method of claim 1, wherein said complex has the formula:

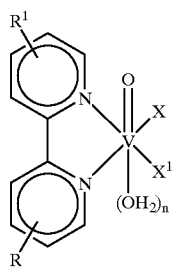

(I)

wherein R, and $R^1$ are the same or different and are each independently: H, lower alkyl, halogen, lower alkoxy, halogenated alkyl, cyano, carboalkoxy or nitro; X and $X^1$ are the same or different and are each independently: monodentate or bidentate ligands; and n is 0 or 1.

5. The method of claim 1, wherein said complex has the formula:

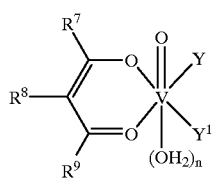

(III)

where $R^7$ and $R^9$ are the same or different and are each independently: H, lower alkyl, lower alkoxy, or halogenated alkyl; $R^8$ is H, lower alkyl, halo, lower alkoxy, or halogenated alkyl; Y and $Y^1$ are the same or different and are each independently: monodentate or bidentate ligands; and n is 0 or 1.

6. The method of claim 2, wherein the bidentate ligand comprises an N, N' bidentate ligand.

7. The method of claim 6 wherein the N, N' bidentate ligand comprises a bipyridyl.

8. The method of claim 7, wherein the bipyridyl comprises a 2, 2' bipyridyl.

9. The method of claim 8, wherein the oxovanadium IV complex is selected from the group consisting of:

(diaqua)(2,2'-bipyridyl)oxovanadium(IV) sulfate;

(aqua)bis(2,2'-bipyridyl)oxovanadium(IV) sulfate;

(diaqua)(4,4'-dimethyl-2,2'-bipyridyl)oxovanadium(IV) sulfate; and (aqua)bis(4,4'-dimethyl-2,2'-bipyridyl)oxovanadium(IV) sulfate.

10. The method of claim 6, wherein the N, N' bidentate ligand comprises a bridged bipyridyl.

11. The method of claim 10, wherein the bridged bipyridyl comprises a phenanthroline.

12. The method of claim 11, wherein the oxovanadium IV complex is selected from the group consisting of:

(diaqua)(1,10-phenanthroline)oxovanadium(IV) sulfate;

(aqua)bis(1,10-phenanthroline)oxovanadium(IV) sulfate;

(diaqua)(4,7-dimethyl-1,10-phenanthroline)oxovanadium (IV) sulfate;

(aqua)bis(4,7-dimethyl-1,10-phenanthroline) oxovanadium(IV) sulfate;

(diaqua)(5-chloro-1,10-phenanthroline)oxovanadium(IV) sulfate; and (aqua)bis(5-chloro-1,10-phenanthroline)oxovanadium (IV) sulfate.

13. The method of claim 6 wherein the N, N' bidentate ligand comprises a diamine.

14. The method of claim 13, wherein the diamine comprises one of phenanthroline and bipyridyl.

15. The method of claim 2, wherein the bidentate ligand comprises and N, O bidentate ligand.

16. The method of claim 15, wherein the N,O bidentate ligand comprises an amino acid functional group.

17. The method of claim 15, wherein the N,O bidentate ligand comprises Schiff base functional group.

18. The method of claim 2, wherein the bidentate ligand comprises an O, O' bidentate ligand.

19. The method of claim 18, wherein the an O, O' bidentate ligand comprises a dicarboxylate compound.

20. The method of claim 18, wherein the an O, O' bidentate ligand comprises a 2-hydroxyacetophenone compound.

21. The method of claim 20, wherein the oxovanadium IV complex comprises bis(5'-bromo-2'-hydroxyacetophenone) oxovanadium (IV).

22. The method of claim 18, wherein the an O, O' bidentate ligand comprises a acetylacetone compound.

23. The method of claim 18, wherein the an O, O' bidentate ligand comprises a catechol compound.

24. The method of claim 3, wherein $X^4$ and $X^5$ comprise monodentate ligands.

25. The method of claim 24, wherein the monodentate ligands are each independently $H_2O$, halide, or carboxylate.

26. The method of claim 3, wherein $X^4$ and $X^5$ together form a bidentate ligand.

27. The method of claim 26, wherein the bidentate ligand is an N, N' bidentate ligand.

28. The method of claim 27 wherein the N, N' bidentate ligand is a bipyridyl or a bridged bipyridyl.

29. The method of claim 28 wherein the N, N' bidentate ligand comprises a bridged bipyridyl, wherein the bridged bipyridyl comprises a phenanthroline.

30. The method of claim 27 wherein the N, N' bidentate ligand comprises a diamine.

31. The method of claim 26, wherein the bidentate ligand comprises an N, O bidentate ligand.

32. The method of claim 31, wherein the N,O bidentate ligand is a ligand comprising an amino acid functional group or a ligand comprising a Schiff base functional group.

33. The method of claim 26, wherein the bidentate ligand comprises an O, O' bidentate ligand.

34. The method of claim 33, wherein the O, O' bidentate ligand is a dicarboxylate compound, a 2-hydroxy acetophenone compound, an acetylacetone compound, or a catechol compound.

35. The method of claim 1, wherein the complex comprises oxovanadium (IV) complexed with at least one of a 1,10 phenanthroline, a 2,2'-bipyridyl, and a 2-hydroxyacetophenone.

36. The method of claim 35, wherein the oxovanadium complex comprises oxovanadium (IV) complexed with at least one monodentate ligand.

37. The method of claim 36, wherein the monodentate ligand is $H_2O$, halide, or carboxylate.

38. The method of claim 4, wherein X and $X^1$ comprise monodentate ligands.

39. The method of claim 38, wherein the monodentate ligands are each independently $H_2O$, halide, or carboxylate.

40. The method of claim 4, wherein X and $X^1$ together form a bidentate ligand.

41. The method of claim 40, wherein the bidentate ligand comprises an N, N' bidentate ligand.

42. The method of claim 41 wherein the N, N' bidentate ligand is a bipyridyl or a bridged bipyridyl.

43. The method of claim 42 wherein the N, N' bidentate ligand comprises a bridged bipyridyl, wherein the bridged bipyridyl is phenanthroline.

44. The method of claim 41 wherein the N, N' bidentate ligand comprises a diamine.

45. The method of claim 40, wherein the bidentate ligand comprises an N, O bidentate ligand.

46. The method of claim 45, wherein the N,O bidentate ligand is a ligand comprising an amino acid functional group or a ligand comprising a Schiff base functional group.

47. The method of claim 40, wherein the bidentate ligand comprises an O, O' bidentate ligand.

48. The method of claim 47, wherein the O, O' bidentate ligand is a dicarboxylate compound, a 2-hydroxyacetophenone compound, an acetylacetone compound, or a catechol compound.

49. The method of claim 5, wherein Y and $Y^1$ comprise monodentate ligands.

50. The method of claim 49, wherein the monodentate ligands are each independently $H_2O$, halide, or carboxylate.

51. The method of claim 5, wherein Y and $Y^1$ together form a bidentate ligand.

52. The method of claim 51, wherein the bidentate ligand comprises an N, N' bidentate ligand.

53. The method of claim 52 wherein the N, N' bidentate ligand is bipyridyl or bridged bipyridyl.

54. The method of claim 53 wherein the N, N' bidentate ligand comprises a bridged bipyridyl, wherein the bridged bipyridyl is phenanthroline.

55. The method of claim 52 wherein the N, N' bidentate ligand comprises a diamine.

56. The method of claim 51, wherein the bidentate ligand comprises an N, O bidentate ligand.

57. The method of claim 56, wherein the N,O bidentate ligand is a ligand comprising an amino acid functional group or a ligand comprising a Schiff base functional group.

58. The method of claim 51, wherein the bidentate ligand comprises an O, O' bidentate ligand.

59. The method of claim 58, wherein the O, O' bidentate ligand is a dicarboxylate compound, a 2-hydroxyacetophenone compound, an acetylacetone compound, or a catechol compound.

60. The method of claim 1, wherein the oxovanadium (IV) complex comprises:

bis(5'-bromo-2'-hydroxyacetophenone) oxovanadium (IV); or (aqua)bis(5-chloro-1,10-phenanthroline)oxovanadium (IV) sulfate.

61. The method of claim 1, wherein the pharmaceutical vehicle is an intravaginal insert.

62. The method of claim 1, wherein the oxovanadium IV complex comprises a complex including a bridged bipyridyl, the complex having the formula:

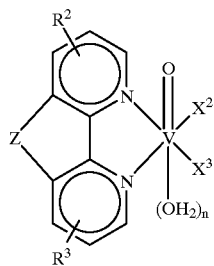

(IV)

wherein $R^2$ and $R^3$ are the same or different and are each independently H, lower alkyl, halogen, lower alkoxy, halogenated alkyl, cyano, carboalkoxy or nitro;

$X^2$ and $X^3$, are the same or different and are each independently monodentate or bidentate ligands; Z is O, $CH_2$, $CH_2$—$CH_2$, or CH=CH; and n is 0 or 1.

63. The method of claim 62, wherein $X^2$ and $X^3$ comprise monodentate ligands and are each independently $H_2O$, halide, or carboxylate.

64. The method of claim 62, wherein $X^2$ and $X^3$ together form a bidentate ligand.

65. The method of claim 64, wherein the bidentate ligand comprises an N, N' bidentate ligand.

66. The method of claim 64, wherein the bidentate ligand comprises an N, O bidentate ligand.

67. The method of claim 64, wherein the bidentate ligand comprises an O, O' bidentate ligand.

68. A method of inhibiting of sperm comprising contacting sperm with an a composition comprising a spermicidal effective amount of an organometallic oxovanadium (IV) complex including at least one bidentate ligand comprising a structure selected from the group consisting of a diamine, an amino acid functional group, a Schiff base functional group, a dicarboxylate, a 2-hydroxyacetophenone, an acetylacetone group, and a catechol group.

69. A method of inhibiting motility of sperm comprising contacting sperm with a composition comprising a spermicidal effective amount of an organometallic oxovanadium (IV) complex comprising at least one substituted or unsubstituted ligand that is a 1,10 phenanthroline; a bridged or unbridged 2,2' bipyridyl; a 2'-hydroxyacetophenone; or a 3-hydroxy-propenal, and a pharmaceutically acceptable carrier, diluent or vehicle.

70. A method of inhibiting motility of sperm comprising contacting sperm with an a composition comprising a spermicidal effective amount of an organometallic oxovanadium (IV) complex selected from the group consisting of:

(diaqua)(2,2'-bipyridyl)oxovanadium(IV) sulfate;

(aqua)bis(2,2'-bipyridyl)oxovanadium(IV) sulfate;

(diaqua)(4,4'-dimethyl-2,2'-bipyridyl)oxovanadium(IV) sulfate;

(aqua)bis(4,4'-dimethyl-2,2'-bipyridyl)oxovanadium(IV) sulfate;

(diaqua)(1,10-phenanthroline)oxovanadium(IV) sulfate;

(aqua)bis(1,10-phenanthroline)oxovanadium(IV) sulfate;

(diaqua)(4,7-dimethyl-1,10-phenanthroline)oxovanadium (IV) sulfate;

(aqua)bis(4,7-dimethyl-1,10-phenanthroline) oxovanadium(IV) sulfate;

(diaqua)(5-chloro-1,10-phenanthroline)oxovanadium(IV) sulfate;

(aqua)bis(5-chloro-1,10-phenanthroline)oxovanadium (IV) sulfate; and bis(5'-bromo-2'-hydroxyacetophenone) oxovanadium (IV).

* * * * *

UNITED STATES PATENT AND TRADEMARK OFFICE
CERTIFICATE OF CORRECTION

PATENT NO.    : 6,337,348 B1
DATED         : January 8, 2002
INVENTOR(S)   : Faith M. Uckun, Osmond D'Cruz and Wanhong Dong It is certified that error appears in the above-identified patent and that said Letters Patent is hereby corrected as shown below:

Title page,
Item [75], Inventors, change "Faith M. Uckun" to -- Faith M. Uckun --.

Signed and Sealed this

Seventh Day of May, 2002

Attest:

JAMES E. ROGAN
*Attesting Officer*   *Director of the United States Patent and Trademark Office*